(12) United States Patent
Agrawal et al.

(10) Patent No.: US 10,302,567 B2
(45) Date of Patent: May 28, 2019

(54) HIGH THROUGHPUT METHODS FOR ANALYSIS OF CONTAMINATION IN ENVIRONMENTAL SAMPLES

(75) Inventors: Anoop Agrawal, Tucson, AZ (US); Juan Carlos L. Tonazzi, Tucson, AZ (US); Lori L. Adams, Tucson, AZ (US); John P. Cronin, Tucson, AZ (US)

(73) Assignee: Berylliant, Inc., Tucson, AZ (US)

( * ) Notice: Subject to any disclaimer, the term of this patent is extended or adjusted under 35 U.S.C. 154(b) by 0 days.

(21) Appl. No.: 12/969,472

(22) Filed: Dec. 15, 2010

(65) Prior Publication Data

US 2011/0092377 A1 Apr. 21, 2011

Related U.S. Application Data

(63) Continuation-in-part of application No. 12/338,724, filed on Dec. 18, 2008.

(60) Provisional application No. 61/008,229, filed on Dec. 19, 2007.

(51) Int. Cl.
*G01N 21/64* (2006.01)

(52) U.S. Cl.
CPC ....... *G01N 21/643* (2013.01); *G01N 21/6452* (2013.01)

(58) Field of Classification Search
CPC .......... G01N 21/643; G01N 21/6452
USPC ................................. 356/301, 382
See application file for complete search history.

(56) References Cited

U.S. PATENT DOCUMENTS

| | | | |
|---|---|---|---|
| 5,055,263 A | 10/1991 | Metzler | |
| 5,459,040 A | 10/1995 | Hammock et al. | |
| 5,463,895 A * | 11/1995 | Brentz ................. | 73/61.71 |
| 5,700,637 A | 12/1997 | Southern | |
| 5,741,463 A | 4/1998 | Sanadi et al. | |
| 5,744,305 A | 4/1998 | Fodor et al. | |
| 5,960,530 A | 10/1999 | Kerr et al. | |
| 7,129,093 B2 * | 10/2006 | McCleskey et al. ......... | 436/79 |
| 7,195,872 B2 | 3/2007 | Agrawal et al. | |
| 7,273,181 B2 | 9/2007 | White | |
| 7,286,061 B2 | 10/2007 | Atkinson | |

(Continued)

FOREIGN PATENT DOCUMENTS

| | | |
|---|---|---|
| WO | WO2007/021679 | 8/2007 |
| WO | WO2008/130737 | 10/2008 |

OTHER PUBLICATIONS

Millipore Website—Description of SLCR013NL Millex-LCR Filter, printer Jan. 5, 2017.*

(Continued)

*Primary Examiner* — Tri T Ton
*Assistant Examiner* — Rebecca C Bryant
(74) *Attorney, Agent, or Firm* — Rothwell, Figg, Ernst & Manbeck, P.C.

(57) ABSTRACT

Use of high throughput methods to analyze samples for toxic elements originating from industrial hygiene and environmental sampling are described. These methods utilize optical detection methods using plates with arrays and microwells. Methods to fabricate samples in such plates are described. The invention is particularly illustrated by demonstrating its applicability for analysis of beryllium by fluorescence and uranium by phosphorescence. This invention also discloses the use of improved filtration method and use of reagents with low background signals.

6 Claims, 11 Drawing Sheets

(56) References Cited

U.S. PATENT DOCUMENTS

| | | |
|---|---|---|
| 7,300,166 B2 | 11/2007 | Agrawal et al. |
| 2001/0055776 A1* | 12/2001 | Greenwalt ........... G01N 33/582 |
| | | 435/7.1 |
| 2002/0028507 A1 | 3/2002 | Heimberg et al. |
| 2003/0027129 A1 | 2/2003 | Warner et al. |
| 2007/0141715 A1 | 6/2007 | McCleskey et al. |
| 2007/0269624 A1 | 11/2007 | Albrecht et al. |
| 2011/0189703 A1* | 8/2011 | Park ............................ 435/7.21 |

OTHER PUBLICATIONS

Ashley et al, Ultra trace determination of beryllium in occupational hygiene samples by ammonium bifluoride extraction and fluorescence detection using hydroxybenzoquinoline, Analytica Chimica Acta, vol. 584 (2007) p. 281-286.

NIOSH Analytical Test Method 7300,: Elements by ICP (Nitric/perchloric acid ashing).

NIOSH Analytical Test method 7703: Chromium, Hexavalent, by field portable spectrophotometry.

NIOSH Analytical test Method 7704: Beryllium in air, by field portable fluorometry.

NIOSH Analytical test method 9110: Beryllium in surface wipes, by field portable fluorometry.

ASTM D7458: Standard test method for determination of beryllium in soli, rock, sediment and fly ash using ammonium bifluoride extraction and fluorescence detection.

\* cited by examiner

HIGH THROUGHPUT METHODS FOR ANALYSIS OF CONTAMINATION IN ENVIRONMENTAL SAMPLES

RELATED APPLICATION/CLAIM OF PRIORITY

This application is related to and claims priority to provisional application 61/008,229 filed on Dec. 19, 2007, which provisional application is incorporated by reference herein. This patent application is continuation in part of U.S. patent application with a Ser. No. 12/338,724 filed on Dec. 18, 2008, which application is incorporated by reference herein.

FIELD OF THE INVENTION

The present invention relates to the detection of contaminants in environmental and industrial hygiene samples using high throughput methods or optical methods. This method can be used to analyze environmental samples of soil, air, water, surfaces and any others for contamination by metals and compounds.

BACKGROUND OF THE INVENTION

U.S. patent application with Ser. No. 12/338,724 was filed on Dec. 18, 2008. The US Government had certain rights in that invention. That invention disclosed the use of multiwell format or using multiwell plates for analysis of environmental samples. The claimed property in this invention and improvements to the multiwell format was not conducted using US Government funds, and hence there are no US Government rights to this invention.

Environmental and industrial hygiene samples originate from a number of places, such as industrial sites, waste storage and dumps, around these areas in air, water and soil, or those that may have been contaminated by terrorist, military or other acts. Some of the toxic industrial materials are lead, hexavalent chromium, cadmium, mercury and beryllium to name a few prominent ones. These materials are typically analyzed by extracting the toxin or the contaminant in a liquid medium (using acids, bases and other solvents and solutions) and then subjecting this to analysis. Typical analysis involves taking these samples and analyzing them sequentially through chromatography (e.g., high performance liquid or gas chromatography), inductively coupled plasma along with atomic emission or a mass spectrometer (ICP-AES and ICP-MS respectively). The samples are eluted into the equipment in a sequence with enough gaps or purges so that there is no cross-contamination. To decrease the labor content and increase the efficiency of the analysis, autosamplers have been developed for such instruments. In these the samples are put in a queue, and the samples are automatically analyzed one after the other. As an example in modern ICP-MS instruments 200 samples may be queued which may take 10 hours to analyze. This causes many issues related to the drift in baseline, and for proper quantification one may require calibration standards to be run periodically during this long analysis time.

The rapid techniques developed in biological analysis lend themselves to high throughput analysis. In these methods the high throughput is obtained in two ways, first by automating the sample preparation and secondly by developing instrumentation that can analyze a large number of samples within minutes. As an example, microarray and microwell formats are routinely used and are then analyzed by optical scanners (by looking for fluorescence, luminescence and absorption/transmission changes and quantifying these). Typical microwell formats have 24, 96, 384 or 1536 or more wells in an area of about 8 cm×13 cm. Such plates can be read by the optical scanners in a matter of minutes. Microarrays may have thousands of analytical spots on a plate. Further, standards occupy some of the spots or wells so that they are all read almost simultaneously (within minutes) avoiding temporal drift.

In addition to be able to read the samples rapidly, it is highly preferable to automate the sample preparation procedures which require repetitive steps of mixing various liquids, filtration, pipetting, and weighing. The purpose of this invention is to enable high throughput analysis of environmental samples and innovate specific steps so that those steps which are unique for our analysis can be conducted in a seamless fashion. This will reduce cost and enable one to take more samples in order to ensure that safety is not compromised due to the throughput issues.

One object of the present invention is to demonstrate that environmental and industrial hygiene samples can be measured at high throughputs.

Another objective of this invention is to enable processes so that environmental and industrial hygiene samples could be prepared by using automatic pipettes configured to work with optical liquid level sensors.

Yet another objective is to automate the sample preparation and analysis to analyze uranium by phosphorescence.

Another objective of this invention is to produce dye solutions with low inherent optical fluorescence which can be used for beryllium analysis using fluorescence by high throughput or any other methods

SUMMARY OF THE INVENTION

In accordance with the purposes of the present invention, as embodied and broadly described herein, the present invention provides a method of preparation of samples and their analysis at high throughputs. This reduces cost, increases efficiency and also reduces chemical waste generated during analysis. This invention is particularly applicable for environmental and industrial hygiene analysis (typically soil, water, air and surface) to analyze toxic elements such as lead, mercury, cadmium, arsenic, beryllium, thallium, antimony, uranium and selenium and other suitable toxic materials.

DETAILED DESCRIPTION

The efficacy of the invention will be primarily demonstrated by many examples for analyzing beryllium by optical fluorescence, but the scope of this invention is also applicable to a number of other environmental toxins.

Beryllium is a metal that is used in a wide variety of industries including electronics, aerospace, defense, and the Department of Energy (DOE) complexes. Exposure to beryllium containing particles can lead to a lung disease called Chronic Beryllium Disease (CBD). Recent new regulations from DOE dictate a permissible exposure limit of 0.2 µg/m$^3$ in air, a housekeeping level of 3 µg/100 cm$^2$ on a surface, and a release level for materials after beryllium exposure where the surface contamination due to beryllium must not exceed 0.2 µg/100 cm$^2$.

Currently, thousands of surface wipes and air filters are analyzed annually for beryllium. In addition Occupational Safety & Health Administration (OSHA) has detected airborne levels of beryllium at numerous sites within the United States. In addition, at some of the sites where past beryllium activity or disposal has taken place, beryllium needs to be cleaned from the soil, down to a level of 131 mg of beryllium in each kg of soil. The popular method for detecting beryllium on a surface involves wiping an area with a filter paper, performing a microwave digestion with acid to dissolute beryllium or its compounds, and then analyzing by inductively coupled plasma (ICP) atomic emission spectroscopy (AES). For analyzing airborne samples, one draws a known quantity of air through a filtering medium and then the filter is treated in a similar fashion to the surface wipes. The ICP-AES technique also requires highly trained operators and the entire sample (typically 5 to 15 ml of solution) is consumed in order to meet the detection levels. If a sample is identified as positive for beryllium then it is difficult to verify with a second run, as most or the entire sample is consumed in the first run. For air filtering one typically analyzes a filter after an eight hour shift. However, in order to protect workers from large instantaneous release of beryllium, the sampling frequency has to be increased which places a greater burden on laboratories using traditional methods. This also affects the sampling frequency for the wipes, where one has to use complex statistics to estimate the thoroughness of the sampling. Such bottlenecks can also be reduced by using the high throughput methods of this invention, where a larger number of samples are analyzed in order to improve confidence in sampling.

Figure 1:
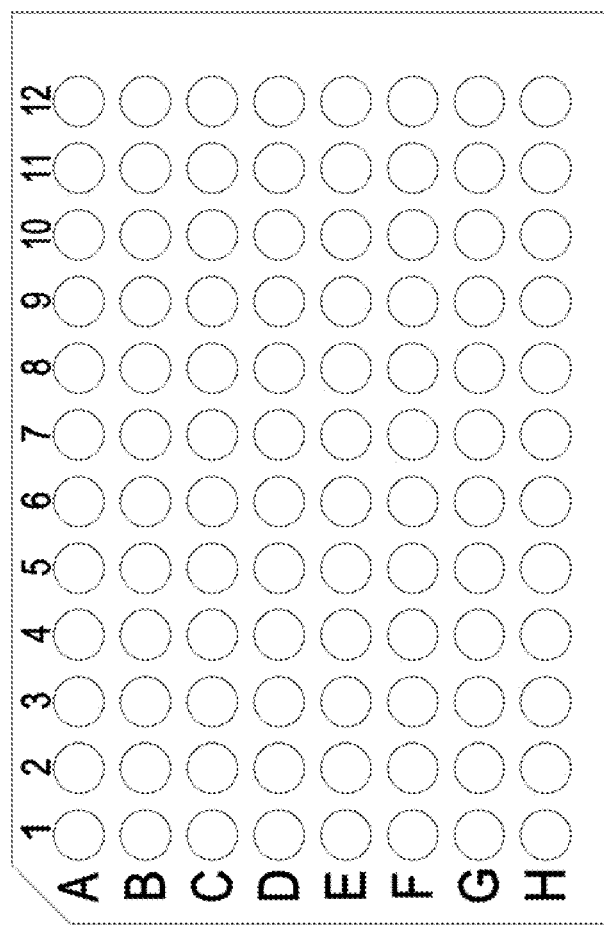
FIG. 1: Schematics of a 96 well plate array.
Figure 2:
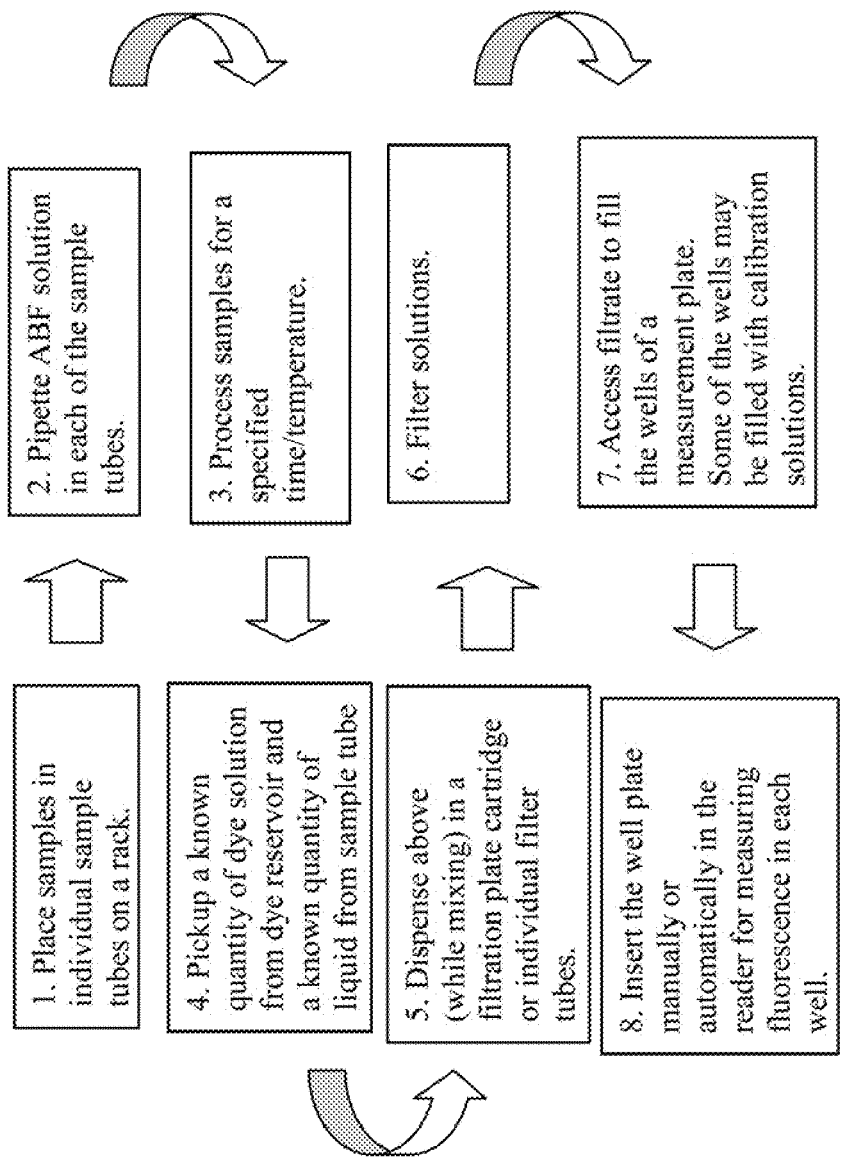
FIG. 2: Schematics of automation for sample preparation for beryllium analysis by fluorescence.

Optical analysis methods such as fluorescence, luminescence and absorption (or change in transmission) have been highly developed for high throughput analysis of biological samples. The fluorescent method for beryllium is well described in U.S. Pat. No. 7,129,093 and US patent application 2005/0221498 and PCT application WO2008/130,737. All of these are incorporated herein by reference. Electron or x-ray induced fluorescence may also be used in an array format. The samples are typically made by attaching fluorescent probes (unless they are self fluorescent) to the biological materials including drugs which are then tested as solids or liquids in an array format. Examples of microarrays can be found in U.S. Pat. Nos. 5,700,637; 5,744,305; and 7,195,872 and US patent application 2003/0027129. Microwells have been used for a long time in biological analysis. Typical plates with microwells are available in standard wells of 24, 96, 384 and 1536 (Fisher Scientific, Pittsburgh, Pa.) where a typical plate size is about 8×13 cm (3×5 inch). Samples in array or microwells can provide a high throughput analysis if the test can be configured to take advantage of this in the field of analytical chemistry. Using an autosampler on an ICP instrument can take almost 6 hours to analyze 90 samples by either AES or MS (Mass Spectrometer), or even using atomic absorption spectrometer (AAS). During this period the calibration curves may shift and one may have to check these periodically extending the analysis time further. As a comparison, a plate with 96 wells (or samples) in a fluorescent system can be read in the order of a few minutes (usually less than 10 minutes, typically less than 1 minute). It is also preferred that some of the wells (typically 4 to 12) are occupied by the standards so that the standards are read at about the same time as the samples, and the unknown concentrations in the samples are detected by calibrating against the standards. The wells holding the calibration standards can be in a particular row or column or be distributed in any order within the plate. This is also different from conventional instruments, where the instrument has to be calibrated first in order to read the samples. In this case all the wells are read for fluorescent intensity, and then the software tool picks out the calibration wells as indicated by the user, fits a curve through it and provides the concentration for the unknown samples. FIG. 1 shows a schematic of a 96 well plate. The rows and columns are designated by a matrix of letters and numbers. For example, well B4 will be the well in the second row of the fourth column. As an example standards can be in a column from A1 to H1 or in A6 to H6, or in a row or in wells distributed throughout the plate. Some of these may be standards for calibration, while the others may be standards to check or verify the accuracy of the results, particularly if some of the results are extrapolated. It is best to use standards in the range of highest interest, and then use some of the wells with predetermined concentrations that are extrapolated and are only of cursory interest. As an example for beryllium since the regulations call for testing from 0.2 to 3 µg, one may use most standards about in this range to get good accuracy. However, to test the accuracy of detection capability or to test if the values are exceeding the highest numbers by a significant amount one may use samples that are 2 to 10 times in excess or less than the highest and the lowest numbers respectively. For example one may use standards corresponding to 5, 1, 0.2, 0.05 and 0 µg for calibrating the range of interest. The samples corresponding to 20 µg and 0.01 µg are also included to check the extrapolation outside the range of highest interest and to check the detection limit of the method respectively. Another way for large dynamic ranges is to calibrate on a log-log scale. Typically this is useful when the range of interest is more than two orders of magnitude (i.e., a difference of 100 times or more). A significant advantage of the optical method is the speed at which the plates or arrays can be read. This allows a laboratory to purchase a single machine which can process thousands of samples that replaces a bank of ICP machines which are highly expensive. Further, in the plate readers one can typically read in a number of formats, i.e. at different wavelengths or different modes such as fluorescence, absorbance, polarized fluorescence, etc. This can be used to provide additional diagnostic tools to eliminate false signals. The false signals can be particularly strong when one is looking at ultralow concentrations, which are typically below 1 ppb (parts per billion) in analytical solutions. As an example, in beryllium analysis by fluorescence the measurement solutions (sample solution mixed with dye solution) can turn yellow. Thus it is important to look at the samples in absorbance/transmittance mode to separate those samples that are yellow in color. The sample yellowness can be typically seen by looking at absorbance anywhere in the range of 400 to 450 nm. Thus an optical filter transmitting in this range can be used to check this. To accurately measure beryllium in such samples, one protocol is to wait for a period of 30 minutes to 6 hours so that the yellow causing compounds precipitate and a re-filtration removes this and the beryllium can be measured. Alternatively, filtering these through hydrophilic filters (e.g. polyether sulfone and hydrophilic polypropylene) without waiting has also shown to be effective.

Further, another serious drawback of conventional methods is the labor involved in sample preparation which adds both to the cost and time. Typically samples are brought to the analytical laboratories in bulk form or as air filters or wipes which are then processed so that the analyte is extracted into a liquid medium. This preparation is usually cumbersome. This may also result in errors and fatigue leading to injury, e.g. Carpal Tunnel syndrome due to repetitive actions such as pipetting. This step can also be automated particularly for preparing arrays or microwell plates. These instruments are available for biological analysis and have not been used advantageously by the analytical, particularly the environmental and industrial hygiene industry.

As a further advantage, the sample requirement of optical methods is small, thus a small fraction of the sample is used for analysis and the rest can be stored to re-check if necessary. As an example, most ICP methods may consume 5 ml to 15 ml of sample where as for optical methods less than 2 ml is required and in many cases less than 1 ml. The 96 well plate readers typically use less than 0.3 ml per well and 384 well plate readers use less than 0.05 ml per well. This also allows one to put several replicates of samples on the same plate to get high statistical accuracy. As an example, in NIOSH (National Institute of Occupational Safety and Health) methods 7704 and 9110, ASTM (American Society of Testing Materials) D7202 methods for beryllium, in general plastic cuvettes are used in which 100 µl of sample and 1.9 ml of dye solution is used. These are small volumes compared to the typical ICP based analytical methods, but these can be reduced further in well format. Smaller volume leads to low amounts of chemical usage and subsequently lower amount of hazardous waste generation as a result of conducting such tests.

One of the several reasons for not automating the sample preparation for typical analytical chemistry methods is the high volumes of liquids that are used for sample preparation in some steps even if smaller samples are used in the final analysis, such as in the beryllium fluorescence method described above. This arises as the sample in the form of a wipe or a filter or bulk soil, one needs larger volumes of these liquids to extract the analyte into the liquid medium. Typically in high throughput methods used in the biological industry, most ingredients are pipetted in 1 ml or lower quantities. In analytical chemistry one requires higher volumes and it is usual to use 5 ml to 100 ml liquids per sample. Another related reason for the lack of automation in the analytical chemistry field is the type of liquids used. In biological assays the liquids used are close to neutral pH (e.g., from about 4 to 9), whereas in analytical chemistry of environmental samples one typically uses strong acids and strong bases with pH usually lower than 2 or pH higher than 10. This becomes difficult to handle in large volumes with system pumps that are generally provided, as these use metals and glass components which can corrode. Use of small disposable pipettes, which generally use dispensable polymeric tips (e.g., polypropylene), are fine with the extreme pH range, but require several operations to dispense large volumes and reduce the throughput of the instrument in terms of samples prepared in a given time. The reason for using smaller pipettes is related to adjusting the spacing between the probes to separation of wells in the standard plates.

Some of the instruments for automated sample preparation are available from Hamilton Inc (Reno, Nev.) as Microstar, model 4200, 4000); from Perkin Elmer (Waltham, Mass.) as Janus; from Tecan Systems Inc (San Jose, Calif.) as Freedom EVO, Genesis; from Velocity 11 (Menlo Park, Calif.) as Bravo, Vprep; from Beckman (Fullerton, Calif.) as Biomek; and from Gilson (Middleton, Wis.) GX and Quad series. All of these have multipurpose robotic functions which may include two or more functions such as picking up and dispensing liquids, filter, mix reagents, weighing, move parts from one place to the other and close or open containers, etc. For high throughput it is better to pump the large volume fluids through the system, so that these can be added to the processing tubes quickly and in one operation. When this is done, these fluids can interact strongly with the materials of construction used. As an example to pump these fluids accurately, glass syringes and metal probes (usually stainless steel) are routinely used. However, in analytical chemistry the use of such materials with strong bases or acids could present problems as most strong acids will attack and corrode stainless steel, and hydrofluoric acid used in many digestions will etch glass. In some cases if the elemental toxin being analyzed is present in small concentration in these probes or syringes (e.g., beryllium in steel and lead in glass), then the results at finer limits may be compromised. Thus it is preferred to replace these with polymeric materials or coat them with polymers to reduce their interaction with the fluids, or use those systems that do not use syringes such as Gilson's GX 281 and GX 271. Preferably the syringes and probes (fine tubes for aspirating in liquids and dispensing them from one place to the other) should be made or coated with organic polymers. Some of the preferred polymers to make these components are polyolefins (e.g., polypropylene), halogenated polymers (e.g., polytetrafluoroethylene and fluorinated ethylene/propylene and polyvinylidene fluoride and polyvinylidene chloride), polycarbonate, polysulphone, polyacetal and polyesters (e.g., polyethylene terephthalate and ethylene naphthalate), and also thermoset polymers such as epoxies and alkyd resins. These polymeric materials along with parylene may also be used for coating metallic or glass/ceramic parts. If coated, these coatings should be placed both on the exterior and the interior surfaces of the probe, while for syringes only the interior surfaces are sufficient. In most preferred cases the probes and the syringes are constructed out of the polymeric materials, with exemplary materials listed above. In some cases it may be desirable to separate steps that require high volume of fluids that are dispensed from those which then take processed samples and prepare small quantities of analyte for final analysis. As an example, ASTM method D7458 is for bulk soil analysis. In this method 50 ml of ammonium bifluoride (ABF) solution is dispensed for each sample and then this is processed by heating and after that only a fraction of a ml of the solution is needed to prepare the final analyte for analysis. Since these vials are large and several liters of ABF solution will be required, it is desirable to preserve space on the expensive multipurpose robotic system and to speed the analysis, a separate simple robotic system is used where the liquid is pumped through for initial pumping of ABF. After processing these vials may be placed on the multipurpose robotic system for preparation of the analyte which requires filtration, mixing with other reagents and preparation of the plate with samples and standards. In case the space on the multipurpose robotic assembly is restricted, one may design a carousel that can feed one or more vials at a time so that the fluid from these can be picked up by the multipurpose robotic probes.

The fluid handling systems may be optionally integrated with liquid level sensors, bar code readers, etc. in order to reduce manual checking and data entry. One may also include a station for automatically weighing the individual samples, where the samples (prior to positioning them in the plates) may be placed robotically. For handling large numbers of samples it is also preferred to use cappers and decappers to easily tighten the caps and remove them from a multitude of bottles or vials used to process the samples. In the fluid handling systems water is typically used as "system fluid" and for washing the reagents as it runs through the system. The "system fluid" is typically degassed before use so that air bubbles in the line do not cause loss of precision and reliability in dispensing which can interfere with the results. For high sensitivity analytical analysis it is preferred that inline degassers be added at the point of entry of system fluid, or in line with each of the fluid channels. For example in line degassers are available from Phenomenex (Torrance, Calif.) under the brand name of Degassex.

Some of the standard methods of use in the industry to analyze toxic materials for the environmental and industrial hygiene applications are given in the table below. Most of these methods use ICP-AES or ICP-MS for analysis.

TABLE 1

| Material to be analyzed | Standard methods using ICP-AES and ICP-MS, AA | Standard Methods using optical and X-ray fluorescence |
|---|---|---|
| Arsenic | OSHA ID105<br>EPA SW846-6010, 6020, 7061, 7062, 7063 | |
| Beryllium | NIOSH 7300, 7102, 7301, 7303, 9102<br>OSHA ID125g, ID206<br>EPA SW846-6010, 6020 | NIOSH 7704, 9110<br>ASTM D7202 |
| Cadmium | NIOSH 7300, 7048,<br>OSHA ID121, ID125g, ID206, ID 289<br>EPA SW846-6010, 6020 | |
| Chromium (Hexavalent) | NIOSH 7605, 7604, 7600, 9101<br>OSHA ID215, W4001<br>EPA SW846-7195, 7197, 7198,7199 | NIOSH 7703<br>EPA SW846-7196 |
| Lead | NIOSH methods 7082, 7103, 7300, 7505, 7701, 9100 and 9105<br>OSHA ID121, ID 125g, ID206<br>EPA SW846- 6010, 6020 | NIOSH Methods 7700, 7702xrf |

TABLE 1-continued

| Material to be analyzed | Standard methods using ICP-AES and ICP-MS, AA | Standard Methods using optical and X-ray fluorescence |
|---|---|---|
| Mercury | NIOSH 6009,<br>OSHA ID140, ID145<br>EPA SW846-6010<br>EPA SW846-6010 | |
| Uranium | | ASTM D5174 |

The present invention is concerned with preparation and analysis of arrays of samples for environmental analysis, which are prepared using automation and read quantitatively by optical methods or by ionizing radiation such as x-rays and electron beams. Typical regulation limits for these materials are summarized in Table 2.

TABLE 2

| Material | OSHA | NIOSH | ACGIH | EPA | DOE |
|---|---|---|---|---|---|
| Arsenic | | | Air<br>10 $\mu g/m^3$ | Water<br>10 $\mu g/l$ | |
| Beryllium (air) | 2 $\mu g/m^3$<br>5 $\mu g/m^3$<br>(Ceiling) | 25 $\mu g/m^3$<br>(Peak) | 0.5 $\mu g/m^3$ | 2 $\mu g/m^3$ | 0.2 $\mu g/m^3$<br>(action limit) |
| Beryllium | | | | Water<br>0.004 mg/l | Surface<br>3 $\mu g/$<br>100 $cm^2$<br>0.2 $\mu g/$<br>100 $cm^2$<br>(Release level) |
| Cadmium | Air<br>5 $\mu g/m^3$ | | Air<br>10 $\mu g/m^3$<br>(total)<br>2 $\mu g/m^3$<br>(respirable) | Water<br>0.005 mg/l | |
| Chromium (Hexavalent) | Air<br>100 $\mu g/m^3$ | Air<br>100 $\mu g/m^3$ | Air<br>100 $\mu g/m^3$ | | |
| Mercury (inorganic) | Air<br>100 $\mu g/m^3$ | Air<br>50 $\mu g/m^3$ | Air<br>50 $\mu g/m^3$ | Water<br>0.002 mg/l | |
| Lead | Air<br>50 $\mu g/m^3$ | Air<br>50 $\mu g/m^3$ | Air<br>50 $\mu g/m^3$ | Water<br>0.015 mg/l | |

ACGIH: American conference of Government Industrial Hygienists'
EPA: Environmental Protection Agency As an example, for beryllium the federal regulations for the Department of Energy (10CFR850) state that airborne contamination in the work space must be less than 0.2 $\mu g/m^3$, which is generally measured by personal samplers (carried by workers in beryllium contaminated area) over an eight hour shift. This is a time weighted average (TWA), where the air is sampled over an eight hour shift and the filter from the sample is then analyzed. Similar standards are established for the other toxins in the work place, particularly for lead, mercury, cadmium and others as listed in Table 1. For example, U.S. Environmental Protection Agency (EPA) standards for water contamination on antimony, selenium and thallium, where the maximum is limited to 6 $\mu g$, 50 $\mu g$ and 2 $\mu g$ in one liter respectively As a first step for most methods, the contaminant is drawn from a solid matrix in a liquid solution (unless the contaminant is already in liquid, such as water). This is done either by dissolution (or extraction of the contaminant or components including the contaminant) or by dissolving of the solid. One may use solutions from known methods to totally digest the sample in order to get the analyte in the solution.

For example, for beryllium, the methods from Environmental Protection Agency (EPA) such as SW846-3051 and 3050, or OSHA125G or NIOSH 7300 use concentrated acid, such as nitric acid, which may be mixed with hydrogen peroxide and concentrated hydrochloric acid, or one may use ammonium bifluoride aqueous solution, as given in NIOSH procedures 7704 and 9110 or ASTM D7202 and D7458.

Although the above acids may be used with this invention, it is surprising that ABF solutions are not used more often in dissolution of other toxins. This is because ammonium bifluoride (ABF) was quite effective in extracting beryllium from metals, oxides and silicates, and secondly it is a one step dissolution process. As an example, NIOSH method 7300 for beryllium calls for treating the samples with a mixture of perchloric and nitric acid on a hot plate at 120 C. More of this acid is added after a small volume is left, and this is repeated several times until the solution is clear. This is then washed with distilled water and heated to dryness at 150 C, and more acid solution is added to dilute the material to a specific amount and then used. This is a multistep process whereas in the ABF treatment, the sample is taken in a tube and a predetermined amount of ABF is added. The solution is then either agitated or heated and at the end of it is filtered for further analysis. This is a single step procedure where several steps of decision making and adding of reagents are not needed to get the analyte in solution. As discussed later, any procedure may be automated; however, one or two step methods are easy to automate at prices that most environmental laboratories can afford. Although ABF aqueous solution has been principally used for beryllium, it may also be used for extracting elemental toxins, such as antimony, lead, thallium, mercury, arsenic, cadmium, selenium, uranium and hexavalent chromium from the media (filter or a wipe) or soils. For each type of sample (air, soil, wipe or the nature of contaminant), the time of treatment, concentration of ABF, temperature of treatment and the ratio of ABF to the sample may vary. However, common protocols are always preferred for automation so that the costs can be reduced. Typically ABF concentrations less than 20% in the solution and a temperature of less than 100 C are adequate for such extractions. For dissolution, the ratio of soil (or the amount of material on the media) to ABF in the solution is preferably less than 1. For example, it has been found that high fired beryllium oxide found in air or that deposits on surfaces in beryllium processing facilities can be dissolved in 1% ABF at 80 C in half an hour in 5 ml solution. Beryllium metal can be dissolved at room temperature under similar conditions in 30 minutes. When beryllium has to be analyzed in soil samples then for 0.5 g of soil sample 3% ABF solution is required at 90 C for 40 hours, and 50 ml of solution is required for half gram of soil samples with particle sizes less than 100 microns (Agrawal, A. et al, Environmental Science and Technology and ASTM test method D 7458). However, in most cases the solvents to extract the toxic metals are acidic in nature (pH is typically less than 4). Since the toxicity of ABF is lower as compared to the concoction of concentrated acids that are used to typically dissolute toxins for environmental and industrial hygiene applications, the use of ABF solutions is desirable.

Multistep dissolution processes may also be automated, where in the dissolution step various optical end point checking techniques may be incorporated. For example, simple absorption or transmittance measurement optics (for example an LED with a detector may be combined) to check the dissolution tubes. The tubes may be located in an oven or a hotblock. The tubes may be capped and these may be decapped and capped automatically in order to add the reagents. Such cappers and decappers are available from FluidX (Cheshire, United Kingdom) and Par Systems (Shoreview, Minn.) and J-KEM Scientific, Inc (Saint Louis, Mo.).

Automated liquid handling systems increase speed, provide consistency in sample preparation and lower cost by reducing the labor. Further, the automation of tasks requiring the repeated manual motion also reduces worker injuries and fatigue. In addition for analysis of radioactive materials such as uranium and thorium it can also provide sample preparation without human intervention to increase the safety.

Hexavalent chromium in NIOSH method 7600 is conducted by dissolution of the chromium from an air filter in an acidic or a basic medium where one uses sulfuric acid to extract soluble chromates and sodium hydroxide and a sodium carbonate mixture to extract insoluble chromates particularly in the presence of reducing agents. Once the final solutions for measurement are made by mixing with diphenylcarbazide, these have to be measured in a period of 2-40 minutes by looking at their absorption at 540 nm. This can present challenges for a large number of samples. Using automated sample processing and utilizing a plate format as discussed above, the consistency of the results can be improved substantially while providing all the benefits listed above.

Lead can also be detected by optical means, e.g., NIOSH analytical method 7700. This looks at development of red color and is a qualitative test. However, using similar principles quantitative tests have been developed such as Hach (Loveland, Colo.) LeadTrak™ system. Use of multiwell plates for analysis and automated sample preparation can expedite any of such test procedures.

As another example uranium is analyzed using kinetic phosphorescence analysis following ASTM method D 5174. Typical range of detection of uranium in samples is 0.01 to 100 parts per million with a detection limit of 1 part per billion. Instrumentation do conduct this analysis is available from Chemcheck Inc. (Richland, Wash.). However, the typical instrumentation used requires sample cuvettes to be made which are analyzed sequentially. According to the present innovation plate based readers could be used and also sample preparation can be automated. In this method uranium from solid samples (e.g. wipes, filters or other media) is first treated with strong acids so that most of the organic matter is destroyed, and the inorganic content becomes soluble in dilute acids. Once the samples reach this stage the rest of the process can be easily automated as that involves. The reading of such plates involves excitation of the sample for a time period which is in about 1 to 100 μs, and then looking at the emission of phosphorescence over a period of time. Since this is done repeatedly on each sample to gather data that is statistically differentiable from one concentration in a sample to another concentration in other sample, it is important that the excitation source can be pulsed. This could be pulsed lasers, however, when multiwell plate readers are used for such an analysis, light emitting diodes and pulsed xenon sources are preferred as these have low maintenance.

As an example, a sequence of automation steps for beryllium using Standardized NIOSH procedures 7704 and 9110 or ASTM D7202 involves the steps as shown in FIG. 1, which involves preparation of a 96 well plate to be read in a fluorescence plate reader.

Step 1: The samples are typically provided in individual tubes which are usually capped. These samples are placed on a rack of the automated system. Preferably the format of the rack should be similar to the multiwell plate that would be made for measurement. As an example, for a 96 well plate a typical format is a matrix of 8 by 12. This rack may be removable or it may be a hot block. Standards may be included in some of the positions on the rack if they will be processed along with the standards. Alternatively, some of the positions may be left blank if standards of known concentrations will be placed in the equivalent positions of the multi-well plate.

Step 2: The samples in the tubes may be a filter paper or a wipe with the sample particles or it may be soil. If the tubes are capped they may be uncapped manually or automatically by the system. After decapping all or one at a time, ABF (dissolution) solution in a known quantity is added to all the tubes. The tubes are then capped (or capped one at a time after adding the reagent)

Step 3: In case the hot block was used as a rack, the program to treat these tubes for a specified time and temperature is initiated, or the rack is temporarily removed for such processing elsewhere. After the samples are processed and cooled, the caps may be removed manually or automatically.

Step 4: The system picks up a specified amount of the fluorescent dye solution from a vial or a tank (or it is run to the probe from the system) and then picks a specified amount of the sample solution from one of the sample tubes, preferably after introducing an air gap (between the two fluids).

Step 5: The two fluids are simultaneously dispensed in a filter cartridge or in a deep well plate with filters placed at the bottom of each well. The fluids may be aspirated and de-aspirated several times for good mixing. The tip is then washed or disposed for the next sample, i.e. steps 4 and 5 are sequentially repeated for all of the samples. If a filter cartridge is used for each individual solution then these are preferably arranged in a similar matrix as the well plates (e.g., 8×12 for 96 well plates), and if a deep well plate with filters is used then this also is preferably for a 8×12 format to go with the microwell plate.

Step 6: If the samples are in individual filter tubes, these may be pressurized so as to filter the contents in a matrix of elution tubes or an elution plate located below the tubes or the filtration cartridge (which ever is used). In the latter typically vacuum is used between the filter and the elution plate for filtration. If any of the compartments in the filtration cartridge are empty they should be filled with a fluid in the same volume as the other wells with samples. A fluid of choice in this case is water.

Step 7: After filtration, the filter tube rack or the filtration plate is removed so that the filtered fluids in the elution plate or the elution tubes is accessible to the probes. A specified quantity of filtrate is removed (typically same quantity for every sample) with disposable or a washable probe into a microwell plate. For 96 well plate this is typically between 100 to 300 µl and for a 384 well plate this is between 20 to 50 µl.

Step 8: Add standards as needed to those microwells in the plate that were reserved for this purpose, and the plate is inserted manually or automatically in a plate reader.

In step 8, standards can be pre-processed, i.e., one may provide a vial comprising a standard concentration which may be diluted in a serial fashion to make concentrations in a desired range. These serial dilutions are then mixed with the dye solution and then dropped on to the wells reserved for the standards in the same volumetric quantity as the samples. All this is done on the same equipment that is used for the sample processing above. The multiwell reading plate may be automatically inserted in the fluorescence reader or it may be done manually. Example 3 provides details of the various processes that were automated in order to achieve the sample preparation and analysis of samples for beryllium analysis provided in the above eight steps. It must be understood that in Example 3, this is an exemplary way of achieving the desired sample preparation and analysis. One could modify these steps in numerous ways to customize the steps for their own needs.

In many of the automation platforms for biological work, one uses disposable plastic pipette tips or reusable metal probes. In the dissolution of environmental samples, the step in which the toxin from the sample is extracted in a liquid media, acidic media or acids are generally used. This requires probes to be highly corrosion resistant. Polymeric probes and tubings are preferred. In order to reduce the cost of the consumables and because probe tips in vastly differing in sizes may be needed to dispense different volumes accurately washable tubings are preferred, i.e. the probe and the tube connecting the pump is a long tubing that will accommodate the largest volume of corrosive liquids to be dispensed. These tubes can dispense small and large volumes that range from several ml down to µl and nl range. It is likely that washable tubings are replaced periodically after they have been used many times. Thus it is important to make these out of materials that are resistant to the solvents used, not easily stainable, easy to clean with the fluids that are permitted with the system, and when it is time for their replacement then it is fast and easy. We have also found that tubes with optical transparency or some translucency are preferred as it is easier to spot the contaminated region. In addition to the visual cue, the calibration and the system performance in reading blanks and low concentrations suffers when the tubes are contaminated.

Some of the preferred materials for the tubing are polyethylene, polypropylene, polytetrafluoroethylene and fluorinated ethylene-propylene, polyvinylidene fluoride, hexa fluoropropylene, chlorinated tetrafluoroethylene, chlorotrifluoroethylene, copolymers of these materials particularly those with at least one monomer being fluorinated, e.g., ethylene and tetrafluorethylene copolymer, vinlyidene fluoride and hexa fluoropropylene, vinyl fluoride and chlorinated tetrafluoroethylene copolymer, and ethylene and chlorotrifluorethylene. As pointed earlier, in one preferred embodiment both the probe and the attached tubing are made out of a plastic and the length of the tubing is adjusted so that the fluids that are picked up by the probe are confined to the tubing only and do not enter the syringes which may have metal or glass parts. The volume of the probe and the tubing is typically 50 ml or less. If metal probes are used they should be preferably coated with acid resistant organic coatings, especially any surface that will come in contact with the acidic solutions. Preferred materials are organic polymeric coatings with low susceptibility to moisture absorption. Some of these materials for coatings are polyethylene, polypropylene, polyvinylidene chloride, parylene and fluorinated polymers, such as tetrafluoroethylene, fluorinated ethylene-propylene and polyvinylidene fluoride, The preferred coatings are typically deposited from vapor phase or from a solution (e.g., from an emulsion). For use with ammonium bifluoride and acids, the most preferred coatings are polyvinylidene chloride and parylene C and parylene D, which are deposited from the solution or vapor phase and are able to coat both the exterior and the interior of the probes.

When probes made out of plastics that are non-conductive (i.e. non electrically conductive), or non-conductive tubing is used as a probe as described above in the automated pipettes for transferring liquids, then one is not able to sense the liquid levels in various wells on different plates or sample solution or calibration solution vials, etc. Liquid level sensing using electrically conductive probes is typically done by capacitive or other electronic changes that the probes sense in proximity of the liquids. Since many of the wells on a plate are in close proximity, and even the probes are in close proximity and move relative to each other to accommodate different distances between wells and sample solution vials, etc, thus any level sensing has to accommodate these close quarters and the relative movement. When there is no level sensing than for all of the equipment programming one has to pay attention to the geometry of the different vials and wells and the amount of liquid present in them or being removed so that these can be accounted for as the probes traverse from one container to the other. Dipping them too deep will unnecessarily subject their exterior to the fluid contamination, and if they are held too high from the dispense point then the liquid addition can cause splash and contaminate the neighboring wells or vials. Thus to simplify this programming level, liquid level sensing mechanism attached to each probe is preferred. For non-conductive probes liquid sensing mechanisms that rely on detecting a change in optical signal (optical sensors) are preferred. The optical sensors are so arranged so that they focus the light very close to the vertical where they are close to the end of the end of the pipette tip or the pipetting end of the tube. Further, this focus point should also be laterally close to the pipette tip so that the smallest of the well size being used in the instrument can be accommodated.

The preferred microwell plates for such analysis are those that have dark sides (preferably black) between the wells. This ensures that there is no optical contamination of signals from the adjacent wells. For fluorescence one may use black bottom plates or those with clear bottom. In the former, the background fluorescence from the substrates is reduced. Typically the excitation source is from the top of the open wells, and the readout is from the top for fluorescence or from the bottom for fluorescence and absorbance. Even with the clear bottoms, it is preferred that these plates have high absorbance for the optical wavelengths used for exciting the fluorescence signal. For beryllium, these plates may have UV absorbers to absorb the radiation below 400 nm. Further, depending on the surface tension of the fluid and the walls, there is a possibility of a shaped meniscus formation at the top, which can focus and bend the incoming light in a fashion that may distort the signal from the well. It is preferred that the wells be either coated with materials to modify the surface tension so that the fluid being analyzed wets the walls of the wells (i.e., the contact angle between the liquid and the modified surface is less than 90 degrees, and more preferably less than 30 degrees). For example, for analyzing aqueous solutions these wells should have a hydrophilic coating, or one may add surfactants to the solutions (as long as this does not interfere with the analysis), to make the sides wetting and keep the meniscus largely horizontal.

Another important aspect of analyzing the well plates is the sensitivity of background to the particulate contaminants that may float on top of the wells giving rise to disturbance in meniscus and also adding to the fluorescent signal depending on the dirt. The automated processing of samples minimizes handling and reduces contamination probability. It is good practice to keep the plates covered when not in use, and handle them with gloves so that oils are not transported on to the plates, which may also add to fluorescence. Insects can have strong fluorescence, and one should examine the plates manually to ensure that bugs have not been trapped in the wells. The disturbance of the meniscus can also be reduced by adding surfactants to the solutions being analyzed. In addition, once the plate is inserted into the chamber, it may be agitated in order to wet the dirt and allow it to sink or minimize disturbances on the surface. One may optionally use a transparent plate (in the optical range of excitation and emission, e.g. quartz) in order to protect the microwells from the dust and other particulates.

Some of the coating methods employed for depositing hydrophilic coatings onto the plates is from vapors and liquids, including chemical vapor deposition processes assisted by plasma. These may be organic or inorganic. Some of the metal oxide coatings that provide hydrophilicity are comprised of silica and titania. These coatings may be comprised of carbon to enhance hydrophilicity. Hydrophilicity may be also imparted by introducing nanopores (pores less than 100 nm in size). One may use precursors such as tetra-orthoethylsilane, methyl triethoxy silane, and adjust the oxygen stoichiometry by introduction of oxygen and ozone (e.g., see WO/2007/021679). Similarly, titanium tetraisopropoxide may be used to deposit hydrophilic coatings of oxide of titanium. Both silicon and titanium precursors may also be mixed (e.g., see Nakamura, et al). These coatings only need to be present near the top rim of the wells where the liquid forms the meniscus in the wells, thus it is not necessary for these coatings to uniformly coat the entire depth of the well. These coatings must be compatible with the solutions being analyzed and should not compromise the analytical aspects.

The surfactants may also be added to the solutions being analyzed. These may be ionic (cationic or anionic) or non-ionic. These are preferably present in quantities of less than 0.1% of the solution volume, and preferably less than 0.01% so as to keep their interactions low. Some examples of such surfactants are Triton® X100, Triton® X-114, Triton® X-405, Novec™ FC4430, Novec™ FC4432, Novec™ FC4434. The first three are available from Aldrich Chemical Co (Milwaukee, Wis.) and the last three from 3M (Minneapolis, Minn.).

A preferred dynamic range for beryllium quantification in surface wipes or air filter samples is less than 0.2 and more than 4 µg on the media, and a more preferred range is less than 0.02 and more than 10 µg on the media and the most preferred range is less than or from 0.005 to 20 µg or more of beryllium on the media. This method has high flexibility to be tailored to any desired range. If higher amounts of beryllium are suspected that go beyond the instrument range, one always has the option to dilute the solutions or to use an optical filter to lower the excitation or the emission intensity. For soils, a preferred range is from about 0.1 µg of beryllium/g of soil to about 2000 µg of beryllium/g of soil, a more preferred range being from about 1 µg of beryllium/g of soil to about 200 µg of beryllium/g of soil.

When samples are analyzed in an array format, it is easy to control the temperature and come to a quick equilibrium, most plate readers have a built in temperature control system in the sample compartment. Since the volume of material used in 96 array format or higher is typically less then 300 µl in each well. Since, air can circulate between the wells it takes a shorter time for the samples to reach thermal equilibrium. Thus it is preferred to use sample volumes of less than 250 µl, and more preferably less than 50 µl. Such analysis also consumes less materials and generates less chemical waste as discussed above The thermal load on the samples is also reduced in an array format, as the optics scan a well for a short period of time, which is typically less than a few seconds, and in most cases a fraction of a second.

Figure 3:
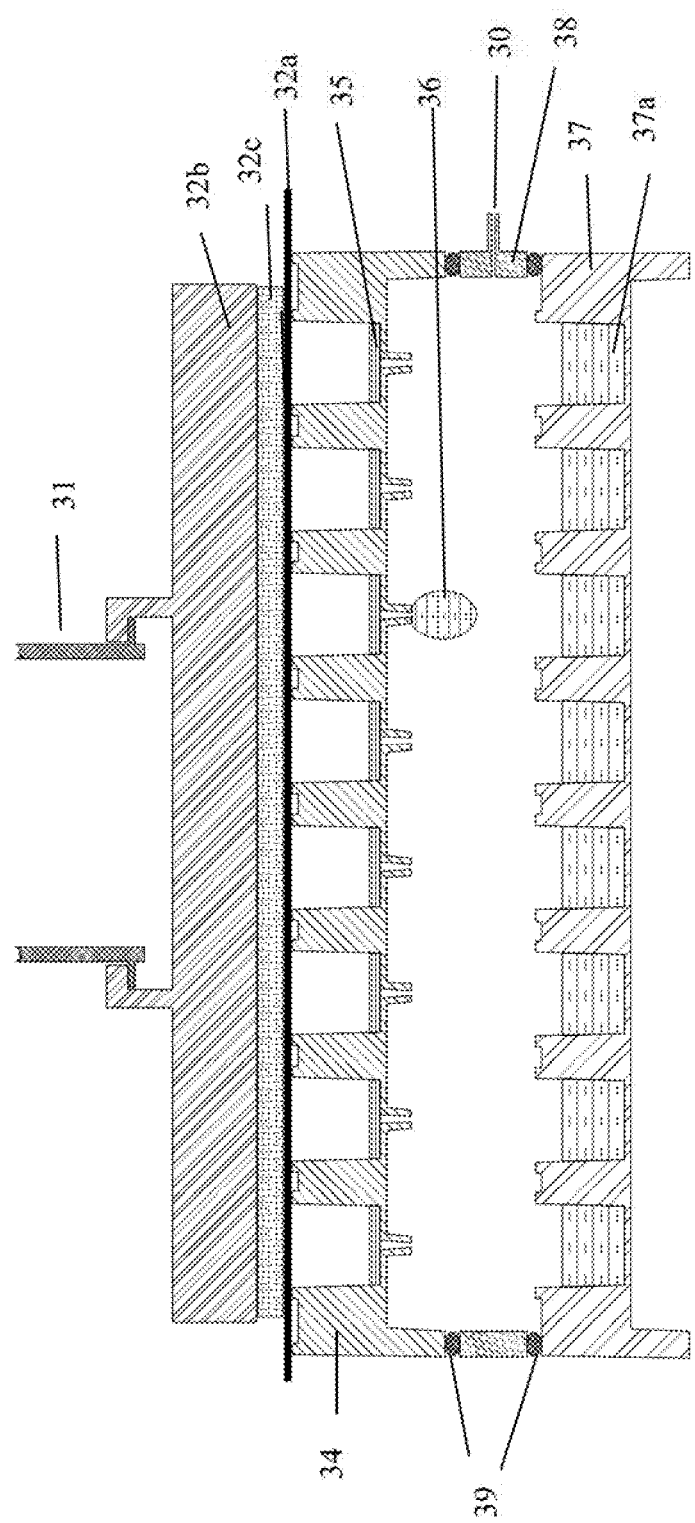
FIG. 3: Schematics of filtration step in automation.
Figure 5:
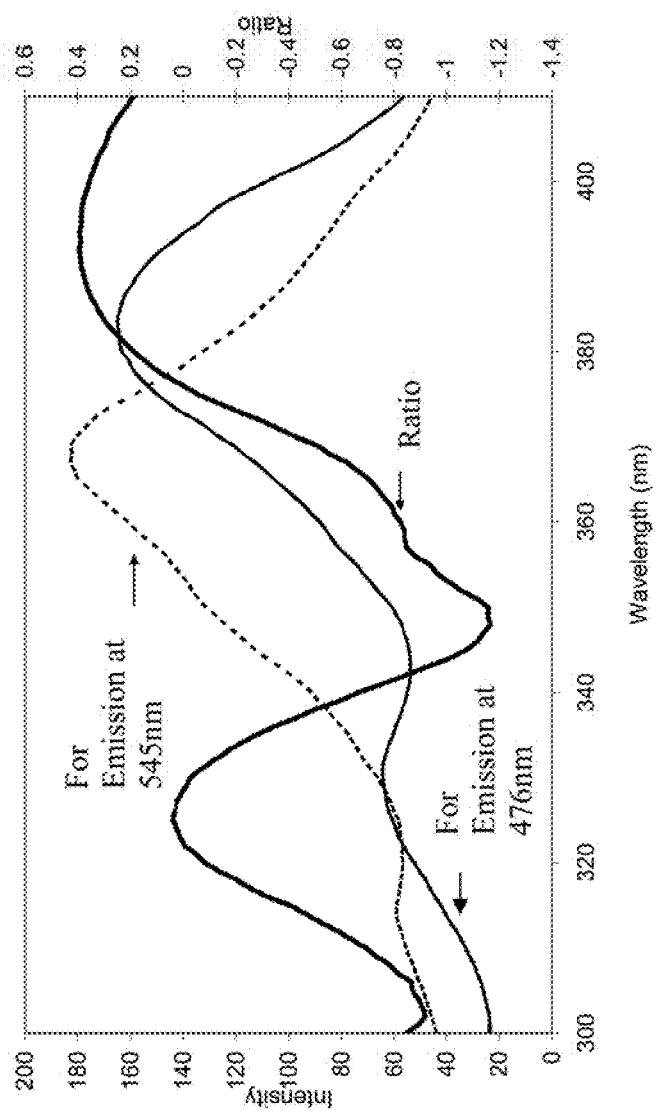
FIG. 5: Excitation spectrum for the peak at 476 nm and at 545 nm for beryllium assay, the ratio of the two spectra is also provided.

Further, a fluorometer equipped to look simultaneously at absorbance and fluorescence is most suited for this method. Absorbance is used to measure the yellowness of the solution to see if the results will be compromised due to the presence of excess iron or titanium. FIG. 3 shows an example of the spectra where the sample has beryllium and iron. If the samples are yellow, one can wait for a period to precipitate so that the solutions can be filtered again (usually through a filter size of less then or equal to 2 microns can be used, a preferred filter used had a pore size of 0.45 microns unless mentioned otherwise). The waiting period is typically between 30 minutes to 6 hours. Alternatively, the measurement solutions may be filtered almost immediately (much smaller waiting times of less than 30 minutes, preferably less then 10 minutes) by filtering through a smaller pore size filter such as smaller than 0.25 microns, preferably less then 0.1 microns. Further, using hydrophilic filtration media, one can eliminate the waiting time. Some of the preferred hydrophilic media are polyether sulfone (PES), hydrophilic polypropylene, etc, In such cases, the preferred filter pore size is smaller than 0.5 µm. As seen in FIG. 5, the yellowness can be measured by measuring absorption or transmission in a wavelength range of 250 to 650 nm, preferably between 350 to 450 nm. The same lamp that is used for excitation may also be used for measuring the absorption with a different detector. Many of the optical plate readers are able to simultaneously read the plates in several modes, e.g., fluorescence and absorbance (e.g., by using clear bottom plates), and since these are fast, they could also read at different regions of the spectrum, allowing multiple analysis to test for anomalies and provide a cross check on the data.

Filtration of liquids in multiwell plates is an important process. FIG. 3 shows a preferred setup for filtration process to achieve complete filtration. The robotic arm of the automated instrument is shown as 31 that assembles and/or disassembles the filtration set-up. The filtration setup comprises of a reservoir plate (37) with wells to contain the filtrate. On top of the reservoir plate, a housing (38) through O-rings (39) connects a filter plate (34). In some cases instead of "O" rings flat joints are also used. This is located with aligned individual filters cells, each having an individual filter (35). For filtration process, vacuum is pulled in the housing (from 30), so that the liquid passes through the filter and is collected in the reservoir plate (37). The vacuum is typically in the range of 25 cm to 55 cm of mercury, with a preferred range being 40 to 55 cm of mercury. At the end of this, all the components above the plate 37 are removed robotically so that the liquid probes can access the filtrate (37a) in plate 37 and continue with the analysis. It is found that at the bottom of several of the filter plate tips a liquid droplet remains (as shown by 36). This is not acceptable, as during the removal of this plate after completing the filtering process, these drops may be released and contaminate liquid in the other wells in the reservoir plate 37. We found that the extent of the problem with hanging droplets was dependent on the filter plate (or multiwell filter plate) that was used which is the material of construction and the geometric configuration of the outlet. To overcome the droplet hanging issue, we found that for some plates, mechanical tapping of the assembly by the robotic arm, or picking the filtration assembly by a few mm and dropping it was also sufficient.

In addition, we also found that in some filter plates all of the liquid could not be filtered completely even with the vacuum assist. In addition as described below, sealing the wells at the top during filtration improved the process. However, we found a very important difference between the filter plates which required sealing at the top and those that did not, further we prefer where those filter plates where the top does not require sealing as it reduces the number of components and steps. Although we used hydrophilic filter membranes, we saw that in some filter plates as soon as liquid was introduced into the wells or soon thereafter, the liquid started to pass through the filter membrane and dripped in the collection well plate below without applying any vacuum (see the discussion of vacuum assist below which is described in relation to FIG. 3). In these filter plates where some of the liquid started passing through the filters soon were not found to be very effective in achieving good filtration. This was also the case when such filter plates were used along with the vacuum assist and showed that in some wells the solution filtered completely while that was not the case for the other wells which were located on the same filter plate. Type A filter plates (or multiwell filter plates) are those where the wells are filled with water and if the water starts dripping through the filter plate in about less than one minute the plates are characterized as leaky filter plates. If the water does not start dripping through the filter plate in about less than one minute the plates are characterized as non leaky filter plates. Type B filter plates were those where this dripping was not noticed in one minute. In more preferred plates this was not noticed even after 10 minutes and in the most preferred plates this number was greater than thirty minutes. In type B filter plates (or multiwell filter plates) application of only vacuum assist as described above was sufficient without sealing the opening of the wells on top of the filter plate. Thus, type B filter plates are highly preferred. These type of plates are called non-leaky plates, and their use is preferred. In Type B plates proper filtration was achieved in all wells even if some had different levels of fluid or were even empty.

To improve filtration in Type A filter plate, so that all the liquid from all of the wells is drained or filtered in the filtration process, we found that sealing the top of the wells in the filter plate (34) was important while the vacuum was pulled for the filtration step. In the past, membranes have been used to cover the top opening of the wells, but they did not effectively seal all the wells to the point that there were no filtration problems. There are sealing membranes available for vacuum assist process to seal the top of the wells of microplates (or microwell plates), such as those from Whatman (Florham Park, N.J.) with a product number 7705-0112. These use a pressure sensitive adhesive sheet so that after the liquid has been added to the wells of the filter plate, this can be placed on the filter plate and then pressed or squeezed in order to seal each of the wells at the periphery, however, this introduces a manual step in the automation where the pressure sensitive adhesive needs to be pressed and rolled several times to ensure good sealing. Further, this manual step can lead to poor sealing if creases are trapped.

This sealing problem can be addressed by employing a plate with individual elastomeric plungers, or plungers with individual O-rings that can seal every well around the perimeter. However, a simple innovative way of overcoming this which could also be implemented automatically was by using a thin elastomeric sheet which was pressed against the wells. In order to make this most effective, it was preferred to combine two sheets of flexible materials in the following way; the thin sealing sheet (first flexible membrane) with a layer of another soft material (32c) called the cushion (second flexible membrane). The cushion helps in transmitting the pressure applied to it uniformly to the first flexible membrane (32a). A preferred way to apply pressure was by a dead weight 32b (e.g. a plate with an appropriate mass). The cushion layer 32c is usually thicker than the element 32a, and may be made out of a flexible open cell foam, closed cell foam, gel or viscoelastic pad or an elastomer generally ranging in thickness from about 0.2 cm and thicker, preferably thicker than 0.5 cm. The element 32c may be bonded to the dead weight 32b. The characteristics of 32a are very important as it needs to seal each of the wells and be flexible so that it does not pucker or crease while sealing. We found good results with elastomeric sheets that were 40 durometer or less in hardness and a thickness less than 1 mm. More preferably durometer 20 or lower and a thickness of 0.5 mm or lower. This allowed the thin elastomer to drape around the top opening of each of the wells without leakage. The element 32c transfers the force from the dead weight or another mechanism more uniformly onto 32a, but does not have to bend with the same degree of precision as element 32a. The thinness of 32a also compensates for any nicks, molding reliefs, flow welds around the well perimeters that are difficult to seal with a thick sheet. Another important parameter was the pressure on this elastomer film. This was greater than 2.5 g/cm$^2$ and preferably greater than 10 g/cm$^2$ of the total filter plate area 34 (including the cross-section of the wells) as projected normally. Some of the preferred materials of construction for 32a are silicone, polyurethane, Viton®, ethylene-propylene diene monomer (EDPM) elastomers, polybutadiene, fluoroelastomers, polychloroprene and polyisoprene. Part 32c can be constructed from a wide variety of materials including the ones described above for 32a as a solid material or as a foam including cellulosic materials and polyolefins (specific examples being, closed cell foams made out of polyethylene, silicone, polyurethanes and ethyl vinyl acetate). The foams should be preferably soft characterized by firmness, typically less than 25% deflection when subjected to a force of less than about 10 psi (typically tested using ASTM method D5672). There may be additional members or sheets with similar or different mechanical properties and thicknesses that may be added between the elements 32b and 32a, and may be optionally bonded together and even to the dead weight to form a composite. It is preferred that the membrane 32a is not bonded to the upper members so that it can deform freely. In order to make the system user friendly, it is preferred that all members (dead weight or pressure plate along with flexible elements other than membrane 32a) are bonded together. Since the bonding assembly will be used several times it is important that all the bonded flexible materials have a high resiliency. Membrane 32a may be replaced after each filtration step or it may be reused. In addition, it may be necessary to slightly restrain the edges of the first membrane (32a) so that this membrane is not pulled in due to the suction created in the wells by the vacuum process in filtration. One method may be too make the membrane 32a long enough so that it wraps around all the preceding elements including the dead weight and then held by removable mechanical clips, magnetic strips or pins so that it is easy made of magnetic material, or magnets or magnetic strips may be attached to it to which the removable magnetic strips/pins can be assembled to. The sealing of the well tops in this invention is particularly good and can be seen when filtering those well plates, where the liquid levels in them is different, or in some wells no liquid is present. This method ensures that the filtration process proceeds smoothly even under these circumstances. In some cases where a good sealing of the wells is not required due to the construction of the multi-well plates, liquids used or otherwise, one may do away with the element 32a, however the use of this membrane results in very high confidence in the filtration process performance. It should be recalled that for type B filter plates the paraphernalia as shown in 32a, 32b and 32c in FIG. 3 is not required.

For analyzing beryllium the standardized methods using optical fluorescence are ASTM D7548 (bulk samples), ASTM D7202 surface wipes and air filters), NIOSH 7704 (air filters) and NIOSH 9110 (surface wipes). Laboratories using these procedures are usually accredited by laboratory certifying agencies, such as American Industrial Hygiene Association (located in Fairfax, Va.). Fluorescent indicator or the dye, 10-hydroxybenzo[h]quinoline-7-sulfonate (10-HBQS) is used in these methods. The buffered dye solution preferably includes a buffer having a pKa between about 7 and 13.5 and more preferably in excess of 12.5. A typical buffer that is preferred is an amine buffer and most preferably is an amino acid such as lysine. Any of the lysine compounds may be used, e.g., D-lysine, L-lysine, DL-lysine, their monochlorides and dihydrochlorides. A preferred lysine compound is L-lysine monohydrochloride. The solution may also contain aminocarboxylates such as ethylenediaminetetraacetic acid (EDTA), diethylenetriaminetetraacetic acid (DTTA), triethylenetetraminehexaacetic acid (TTHA), and the like, or salts thereof, as a chelating agent to bind metals other than beryllium. Preferred salts of EDTA are EDTA dipotassium dihydrate and EDTA disodium dihydrate. Other chelating agents such as aminophosphonates may be used as well. There are a few preferable choices of indicators, all of which are based on forming six-member rings with the beryllium ion bound to a phenolate oxygen and a pyridine nitrogen. In these test methods a small aliquot of the sample solution (where beryllium has been extracted from the media-bulk, wipe or air filter) is mixed with the dye solution in a certain proportion and its fluorescence evaluated under specific optical excitation and emission conditions.

For the beryllium method using fluorescence the sensitivity can be increased by changing the ratio of the sample containing dissolution solution and the dye solution. In U.S. Pat. No. 7,129,093, the volumetric ratio of the dissolution solution (comprising beryllium) to the detection solution (comprising dye) was 1:19. We found that ratios higher than 1:19 may be used to increase the detection limit of the method while keeping the other parameters constant. Increased ratios result in more beryllium in the detection solution thus increasing the sensitivity (lowering the detection of beryllium on the original media) of the method. Ratios higher than 1:12, e.g. such as 1:4 may be used to increase the beryllium content in the "measurement solution" by four times (see published US patent application 20050280816). Use of dilution modification to increase sensitivity has been published by Ashley et al, in Analytica Chimica Acta in 2007. The automation for any dilution (e.g. 20× or 5× or a number in between) can be easily achieved by change of a software protocol. Several methods can be provided for the user to select. Since only a small quantity of the sample is used, both protocols can be run automatically, or sequenced so that if no beryllium is detected (or detected below a certain level) a separate assay is run for these using a 5× dilution.

For beryllium analysis using HBQS dye (see Example 15 for the details of the ingredients used in the dye solution), a preferred excitation a range is between 365 to 395 nm. This maximizes the emission signal response between 470 and 480 nm and maintains good linearity. Two kinds of fluorescent instruments are used which can be differentiated from their optics. In one, the monochromators are used for the user to select the wavelength of excitation and emission, in the second fixed optical filters are used to only allow specific wavelengths to pass through, thus the user needs to have such optical filters at hand. For filter based readers an excitation filter transmitting with a peak located between 380 and 390 nm with a bandpass of equal or less than ±20 nm, preferably less than or equal to ±10 nm results in high excitation. For emission, the peak transmission in the range of 470 to 480 with a bandpass of ±5 nm to ±20 nm is preferred. The maximum transmission of the emission filter should be as high as possible, and is preferably greater than 50% and more preferably greater than 90%. For example, a preferred filter will have a peak transmission at 475 nm with a bandpass of ±20 nm and the maximum transmission at the peak above 90%. The most preferred filter will have a plateau in the peak transmission area, with the transmission dropping to about 0% in about 2 nm on either side of the curve. The transmission at the peak should be preferably greater than 50%. The optical density of emission in the non-transmissive areas should have an optical density of four or greater, and more preferably 6 or greater to minimize light leakage from excitation and also to ensure that fluorescence signals outside of the desired range do not contribute to the desired signal.

Another, factor that leads to improvement in ultra-low detection is reducing the background fluorescence. Background fluorescence from the HBQS buffered dye solution (as described earlier) in beryllium analysis by fluorescence may be substantially reduced by using higher purity materials, such as lysine, that produce fluorescence due to inadvertent impurities found in commercial materials. In a most preferred mode a dye solution made according to the recipe in standard (or standardized) test methods such as, NIOSH test method 7704 or NIOSH test method 9110 or ASTM D7202 or ASTM D7458 should not have any fluorescence background when the dye solution is tested as a sample (i.e. without any added beryllium) in these test methods. To test the dye solution, the instrument is calibrated to give ppb (parts per billion) readings of beryllium. On this scale the low fluorescent dye solution should have the ppb reading equal to or less than 0.1 ppb beryllium, more preferably equal to or less than 0.05 and most preferably 0.01 or less. Also, it should be pointed out that in order to follow the procedures of the currently allowed standardized test procedures, the changing of dye concentration in the solution for lowering the fluorescence will be a deviant which is a less preferable approach, and further does not result in as much background reduction as achieved by using high purity lysine. However, using high purity materials will lower the background fluorescence for any approach that is taken, including changing the dye concentration if needed.

In NIOSH method 7703, hexavalent chromium is analyzed using absorption at 540 nm. For this test clear bottom plates are used for analyzing these on a plate reader. In sample preparation step centrifugation can be easily accommodated in the automation for liquid handling as in the biological systems from Tecan (Durham, N.C.), Velocity 11 (Menlo Park, Calif.), Perkin Elmer (Waltham, Mass.) and others. Further after diphenylcarbazide is added there is a window of about two to forty minutes in which the sample must be analyzed. With manual methods it becomes difficult to control this time. In automated system, the addition of this material to the chromium comprising samples can be accomplished in minutes and transferred to an automated shaker (several plate readers have built in shakers as well e.g., Biotek's (Winooski, Vt.) Synergy 2 instrument), and then all the samples analyzed within minutes, thus increasing the precision of the measurements. For hexavalent chromium, typical limits established by various agencies in air are from 0.1 to 0.001 mg/m3.

EXAMPLE 1: TREATMENT OF STAINLESS STEEL PROBES FOR INCREASED CORROSION RESISTANCE

Stainless steel needles and discs were exposed to 3 weight % ammonium bifluoride solution in water at both 25 and 90° C. The stainless needles were unprotected whereas the discs were coated with a protective material by Restek Performance Coatings (Pittsburgh, Pa.) namely Silosteel-CR. Silosteel-CR is a corrosion resistant layer that increases the lifetime of materials in acidic environments. The two forms of stainless steel were soaked in the ammonium bifluoride and their weight monitored with time. The results are summarized in Table 3. As seen in the table all samples did not do well and were corroded by ammonium bifluoride. At 90° C. the sample with Silosteel-CR layer lost 4 weight % and the soaking solutions turned green in color.

TABLE 3

| Sample Material | Soaking Temp. (° C.) | Time left soaking (hrs) | Initial Weight (g) | Final Weight (g) | Δ Weight (g) | % Weight loss | Comments |
|---|---|---|---|---|---|---|---|
| Stainless steel needle | RT | 112 | 0.11626 | 0.11315 | 0.00311 | 2.7 | Needle is corroded, ABF solution is colorless |
| Stainless steel needle | 90° | 112 | 0.11440 | 0.07621 | 0.03819 | 33.4 | Needle is corroded, ABF solution is green |
| Stainless steel disc With CR coating | RT | 24 | 7.78184 | 7.77656 | 0.00528 | 0.07% | Disc is unchanged |
| Stainless steel disc with CR coating | 90° | 24 | 7.76427 | 7.46242 | 0.30000 | 4.0% | Disc is corroded, ABF solution is green |

EXAMPLE 2: COATING WITH PARYLENE TO IMPROVE CORROSION RESISTANCE

Stainless Steel coupons were coated with Parylene using a vapor deposition process. The type of parlyene used was "C" and the coating thickness was 2.5 microns. The coatings were deposited to MIL-1-46058C specifications by Advanced Coating (Rancho Cucamonga, Calif.). The coupons were tested in 3 weight % ammonium bifluoride at 25 and 90° C. and after 48 hours showed a slight increase in their weight due to water uptake of the polymer coating. The results of the test are shown in Table 4 and show that after 48 hours the stainless steel coupons were completely protected from corrosion by the polymer coating. In all cases the soaking solution remained colorless.

TABLE 4

| Sample # | Initial Weight (g) | 48 hour Soak Final Weight (g) |
|---|---|---|
| 25° C. Soak | | |
| K442A | 0.19793 | 0.19797 |
| K442B | 0.2094 | 0.20945 |
| J887 | 0.19408 | 0.19413 |
| K462 | 0.40903 | 0.40905 |
| 90° C. Soak | | |
| K052B | 0.1634 | 0.16368 |
| K442B | 0.44011 | 0.4699 |
| J887 | 0.18734 | 0.1909 |

EXAMPLE 3: PROGRAMMING ROUTINES FOR THE HT EQUIPMENT TO ANALYZE BERYLLIUM IN SAMPLES BY OPTICAL FLUORESCENCE USING STANDARD METHODS

In order to automate the sample preparation and analysis of beryllium using NIOSH method 7704 and 9110 and ASTM D7202, we chose a robotic platform Janus™ from Perkin Elmer (Waltham, Mass.) and a plate reader from BioTek (Vinooski, Vt.) called Synergy 2™. We decided to write three independent routines. In the first routine (ABF Dispensing), ABF is dispensed in an array of sample vials. In the second routine (Calibration standard preparation), calibration solutions are prepared with different concentrations of beryllium from a stock solution. In the third routine (Plate preparation and analysis) the machine prepares a microwell (or multiwell) plate for measurement of beryllium and carries the plate over to the reader so that it can be read. These programs can be run in any order as desired by the user so that the user is able to optimize the use of time and resources depending on their specific needs.

For example an user may start out with the first program by adding 5 ml of ABF solution to each of the sample vial. At the end of the process the sample tray is removed and typically the samples are heated to extract beryllium from the samples into the ABF solution. Meanwhile as this sample tray is being processed, the user can prepare another sample tray by adding ABF, or could prepare a series of calibration solutions, or using a previously processed sample tray (where the extraction process has been completed) start producing a microwell plate for measurement. Detailed steps that the machine is programmed for each routine are listed below. These details are not unique but only a representation of an exemplary implementation of the method.

Since ABF is corrosive to metals and glass, and since we preferred using glass syringes were used in the pump, the tubes were of sufficient length to accommodate the maximum amount of ABF that it would aspirate and then dispense in sample vials. We did not want to use ABF as one of the system fluids so that it could be dispensed without aspirating for the corrosivity reasons. Since the tubes used were made of corrosion resistant plastic these were used both as the tips and the reservoir for ABF solution up to 5 ml in volume. The internal diameter of the tubes was 0.15 cm which for each 30 cm (or one foot) had a volume of 0.53 ml. Thus to accommodate 5 ml volume with an extra room the tube length that was chosen was 360 cm (or 12 ft long). One end of this was tapered through which pipetting was done and the other end was connected to the pump. Thus there were four tubes for each of the four pipettes in this instrument.

ABF Dispensing
1. A sample rack, usually in an 8×12 format, is placed on the deck of the robotic dispenser. The rack may have only 80 samples of filters or wipes placed in empty tubes. In this case, the other places in the rack are left empty.
2. All four tips are flushed and washed with distilled water by pumping water through the tubing. In the wash step the dispensed water is swirled up around the outside of the tips to clean them.
3. The four tips pick up 5 ml of ABF solution from the ABF reservoir at the same time and deliver that to four of the sample tubes. The tips are slightly dipped in the dispensed ABF to wick off any ABF droplets that are left behind.
4. All four tips are again flushed and washed with distilled water.
5. Steps 3 and 4 are repeated until ABF solution is added to all the tubes.

Calibration Standard Preparation
1. Two standard trays, usually in a 6×4 format, are placed on the deck of the robotic dispenser. The trays are loaded with empty tubes, typically with a capacity of 1.5 ml. These are used to prepare and store calibration solutions with different amounts of beryllium using serial dilution from a single beryllium standard, usually 4000 ppb Be for the 20× dilution and 800 ppb Be for the 5× dilution.
2. All four tips are flushed and washed with distilled water by pumping water through the tubing. In the wash step the dispensed water is swirled up around the outside of the tips to clean them.
3. Only one tip, usually tip#1, is used in the serial dilution part of this preparation. First, ABF is aspirated, followed by the aspiration of air to form a small air gap. Next the stock calibration solution to be diluted is aspirated, again followed by an air gap. This liquid is then dispensed into an empty tube and the dispensed liquid is mixed by aspirating and dispensing the liquid several times, usually at least three times, in the tube. The ratio of ABF to the stock calibration solution varies depending on the desired resulting standard.
4. The tip being used for the serial dilution is flushed and washed with distilled water.
5. Steps 3 and 4 are repeated where the next dilution is performed by using the diluted stock solution from the previous step, until the desired serial dilution sequence is completed.
6. All four tips are again flushed and washed with distilled water.
7. All four tips pick up detection solution from a reservoir and dispense that into four empty samples tubes at the same time. The tips are slightly dipped into the dispensed detection solution to wick off any droplets. The amount of detection solution is the same for all of the standards prepared, but varies depending on the amount of standard desired and on whether the standards are for a 20× or a 5× dilution.
8. All four tips are again flushed and washed with distilled water.
9. Steps 7 and 8 are repeated until detection solution is added to all the tubes, usually sixteen.

10. All four tips are again flushed and washed with distilled water.
11. All four tips aspirate a blank stock solution from a tube on one of the sample trays in the correct volume needed. The blank solution is dispensed into the tubes that already contain the detection solution. Again, the tips are slightly dipped into the solution to wick off any droplets.
12. The dispensed liquid is then mixed by aspirating and dispensing the liquid several times, usually at least three times, in the tube.
13. All four tips are again flushed and washed with distilled water.
14. Steps 11, 12 and 13 are repeated until the desired number of blank standards are prepared, usually six.
15. All four tips are again flushed and washed with distilled water.
16. All four tips aspirate stock solutions, in the correct volume needed, from the tubes containing the serial dilution standards prepared earlier. The stock solutions are dispensed into tubes that already contain the detection solution. Again, the tips are slightly dipped into the solution to wick off any droplets.
17. The dispensed liquid is then mixed by aspirating and dispensing the liquid several times, usually at least three times, in the tube.
18. All four tips are again flushed and washed with distilled water.
19. Steps 16, 17 and 18 are repeated until the desired numbers of standards are prepared, usually about ten. Note that the six blanks prepared in step 14 and the ten standards prepared here make up the total of 16 calibration standards that are typically prepared.

Plate Preparation and Analysis

1. A sample rack (usually in an 8×12 format, containing about 80 samples which have been extracted into the ABF solution), two standard trays (usually in a 6×4 format), a 96 well filter plate (usually 2 ml), two 96 deep well plates (usually 1 ml), a 96 well read plate (usually 300 µl), and a vacuum manifold are all placed on the deck of the robotic dispenser.
2. The robotic arm assembles the filtration assembly by stacking the vacuum manifold, a 96 deep well plate and a 96 well filter plate.
3. All four tips are flushed and washed with distilled water by pumping water through the tubing. In the wash step the dispensed water is swirled up around the outside of the tips to clean them.
4. All four tips pick up detection solution from a reservoir and dispense that into four empty wells on one of the 96 deep well plates at the same time. The tips are slightly dipped into the dispensed detection solution to wick off any droplets. The amount of detection solution is the same for all of the samples prepared, but varies depending on the amount of sample desired and whether the samples are for a 20× or a 5× dilution. For a 1 ml deep well plate the usual amount of detection solution for the 20× dilution is 950 µl and for the 5× dilution is 800 µl.
5. All four tips are again flushed and washed with distilled water.
6. Steps 4 and 5 are repeated until detection solution is added to all the wells being used, usually 80 or less. (This number matches the number of ABF samples that have been processed).
7. All four tips are again flushed and washed with distilled water.
8. All four tips are used to transfer four samples extracted into ABF solution from the tubes on the 8×12 rack to four wells in the deep well plate that have been filled with detection solution in step 4 above. The tips are slightly dipped into the solution to wick off any droplets. The amount of sample dispensed is the same for all of the samples prepared, but varies depending on whether the samples are for a 20× or a 5× dilution. For a 1 ml deep well plate the usual amount of sample for the 20× dilution is 50 µl and for the 5× dilution is 200 µl.
9. The dispensed liquid is then mixed by aspirating and dispensing the liquid several times, usually at least three times, in the well.
10. All four tips are again flushed and washed with distilled water.
11. Steps 8, 9 and 10 are repeated until the desired number of samples are prepared, usually 80 or less.
12. All four tips are again flushed and washed with distilled water.
13. All four tips are then used to aspirate four standards from the 6×4 standard trays, usually 1 ml, and dispense them into four empty wells of the 96 well filter plate.
14. All four tips are again flushed and washed with distilled water.
15. Steps 13 and 14 are repeated until all of the standards, usually 16, are moved to the filter plate.
16. All four tips are again flushed and washed with distilled water.
17. All four tips are then used to aspirate four samples from the 96 deep well plate, usually 1 ml, and dispense them into four empty wells of the 96 well filter plate.
18. All four tips are again flushed and washed with distilled water.
19. Steps 17 and 18 are repeated until all of the samples, usually 80 or less, are moved to the filter plate. Note that if 80 samples are transferred in this step and the 16 standards were transferred in step 15 then this would completely fill the 96 well filter plate. However, all 96 wells of the filter plate do not need to be filled for the filtration step.
20. All four tips are again flushed and washed with distilled water.
21. The samples and standards are then vacuum filtered into a 96 deep well plate.
22. The filter assembly is then taken apart and all four tips are again flushed and washed with distilled water.
23. All four tips are then used to aspirate four filtered samples and standards from the 96 deep well plate, usually 230 µl, and then dispense them into four empty wells of the 96 well read plate.
24. All four tips are again flushed and washed with distilled water.
25. Steps 23 and 24 are repeated until all of the filtered standards and samples have been dispensed into the 96 well read plate.
26. The 96 well read plate can be moved to the plate reader either automatically using the robotic arm or manually. The plate is then read by the plate reader and is either automatically or manually moved back to the deck on the robotic dispenser.

EXAMPLE 4: RESULTS FROM ANALYSIS OF BERYLLIUM IN SAMPLES USING HT EQUIPMENT USING LINEAR CALIBRATION

The Standardized methods ASTM D7202 and NIOSH methods 7704 and 9110 using fluorescence for detecting beryllium was adapted for a fluorescence reader using a 96 well plate. The reader was a BioTek Synergy 2 fluorescence plate reader and the plate was a Corning Costar 3915 flat bottom non-treated non-sterile, black, polystyrene 96 well assay plate. The plate format was such that the 8 wells in the first column contained the beryllium standards and the remaining wells contained the unknowns. The excitation filter used was 365±10 nm and the emission filter was 476±3.5 nm. The light source was a tungsten lamp and readings were taken from the top of the well (50 readings/well) with a mirror optics position of 400 nm.

Beryllium Standards Preparation

The standards used to calibrate the BioTek reader were 0, 0.1, 0.5, 2.0, 10.0, 40, 100.0 and 200.0 ppb and the volume in the well was 230 µL. These were plotted in a linear form and a regression fit was used to calculate the correlation value R. Values of R 0.999 were considered a good fit. The 0, 0.5 2.0 10.0 and 40.0 ppb calibrants were prepared by a 20× dilution of the following beryllium standards: 0, 10, 40, 200, 800 ppb supplied by Spex CertiPrep Metuchen, N.J. An example of the calibrant preparation is as follows: 0.1 ml of the Spex standard was dissolved in 1.9 ml of the HBQS dye detection solution (20× dilution) and 230 µL of this solution was placed in the well. Some of the other standards from SPEX were diluted with 1% ABF and then diluted 20× with the dye solution to obtain calibrants with 0.05, 0.1 and 200 pp of beryllium. In these standards the source of beryllium was beryllium acetate.

Analysis

The samples in the plate were solutions containing known beryllium acetate concentrations in the range 0.05 to 200 ppb. The complete 96 well plate was read in a dual format where samples with beryllium ≤40 ppb were read using a "Fine" standard calibration curve based on 0, 0.1, 0.5, 2.0, 10.0 and 40 ppb standards and samples with "Coarse" beryllium content ≥40 pb) where read using 40, 100 and 200 ppb standards. This was achieved by programming the reader to read the well plate using the "Fine" and the "Coarse" standard calibration curves. For the "Fine" calibration reading the voltage was set at 145 volts which was equivalent to 1.76 million counts for the 40 ppb standard. For the "Coarse" readings the voltage was set at 120V, which is equivalent to 1.89 million counts for the 200 ppb well. At 50 reads per well and performing the dual measurement, it took 8 minutes to read the complete plate with 96 wells. The results for the "Fine" and "Coarse" measurements are shown in Table 5. According to the Standardized procedures, 0.05 ppb corresponds to 0.005 µg on the air filter or the wipe and 200 ppb corresponds to 20 µg.

Readings of standards against the calibration are shown

The data from the above table is summarized in Table 6 where the mean and standard deviation of the values are shown. The mean for the 0.05 to 2 ppb is based on readings from 24 wells and for the 200 ppb sample it is based on 16 wells.

TABLE 6

Mean and Standard Deviation of the Unknown Beryllium Samples

| Sample | Mean (ppb) | Standard Deviation |
|---|---|---|
| 0.05 ppb | 0.056 | 0.007 |
| 0.1 ppb | 0.121 | 0.038 |
| 2 ppb | 1.99 | 0.051 |
| 200 ppb | 202.631 | 2.184 |

EXAMPLE 5: RESULTS FROM ANALYSIS OF BERYLLIUM IN SAMPLES USING HT EQUIPMENT USING LOGARITHMIC CALIBRATION

A 96 well plate similar to that described in Example 4 was read on the BioTek reader where the calibration curve used (standards same as in Example 4) was plotted on a log-log scale. Using this scale all standards could be read in one reading which eliminated the need to do the dual scan of the low and high standards. For 50 reads/well the time to scan the plate was 4 minutes. For this reading the excitation filter was 365±5 nm, the emission filter was 476±3.5 nm and the sensitivity was set at 85V which is equivalent to 1.45 million counts for the 200 ppb sample. The results for this analysis are summarized in Table 7 in terms of mean and standard deviation.

TABLE 7

Mean and standard deviation for readings based on log-log standard calibration plot

| Sample | Number of Wells | Mean (ppb) | Standard Deviation |
|---|---|---|---|
| 0.05 ppb | 8 | 0.05 | 0.008 |
| 0.1 ppb | 8 | 0.103 | 0.008 |
| 0.5 ppb | 8 | 0.536 | 0.025 |
| 2 ppb | 16 | 2.056 | 0.052 |
| 10 ppb | 8 | 9.712 | 0.252 |
| 40 ppb | 16 | 41.105 | 0.794 |
| 100 ppb | 16 | 93.765 | 2.908 |
| 200 ppb | 8 | 191.856 | 2.857 |

TABLE 5

Readings from a plate comprising of standards and samples

| | 1 | 2 | 3 | 4 | 5 | 6 | 7 | 8 | 9 | 10 | 11 | 12 |
|---|---|---|---|---|---|---|---|---|---|---|---|---|
| A | 0 (0) | 0.072 | 0.055 | 0.06 | 0.124 | 0.142 | 0.137 | 2.021 | 2.073 | 2.049 | 203.2 | 204.1 |
| B | 0.092 (0.1) | 0.061 | 0.057 | 0.058 | 0.108 | 0.102 | 0.108 | 2.08 | 2.004 | 2.009 | 205.0 | 203.8 |
| C | 0.51 (0.5) | 0.056 | 0.073 | 0.056 | 0.111 | 0.256 | 0.119 | 2.01 | 1.991 | 1.977 | 200.7 | 203.7 |
| D | 1.895 (2) | 0.053 | 0.06 | 0.056 | 0.102 | 0.115 | 0.102 | 1.97 | 2.016 | 1.997 | 202.8 | 200.2 |
| E | 9.947 (10) | 0.055 | 0.053 | 0.058 | 0.108 | 0.103 | 0.104 | 1.984 | 1.989 | 1.96 | 200.7 | 200.6 |
| F | 39.969 (40) | 0.052 | 0.049 | 0.067 | 0.107 | 0.107 | 0.108 | 1.972 | 1.893 | 1.949 | >208. | 199.0 |
| G | 100.5 (100) | 0.046 | 0.043 | 0.06 | 0.223 | 0.106 | 0.106 | 1.954 | 2.099 | 1.951 | 206.6 | 203.5 |
| H | 199.8 (200) | 0.053 | 0.05 | 0.05 | 0.1 | 0.106 | 0.109 | 1.901 | 1.976 | 1.932 | 205.0 | 200.7 |
| | Stds* | | 0.05 | | | 0.1 | | | 2 | | 200 | |

*Wells A1 to H1 had standards that were use to calibrate and quantify the other wells.

EXAMPLE 6: IMPROVING THE CONSISTENCY OF THE MENISCUS IN THE MICROWELLS

To modify the wetting of the samples and standards in the polystyrene wells a surfactant, namely Triton-X100, available from Sigma-Aldrich (Milwaukee, Wis.), was added to the solutions. The surfactant was added to the detection solution in a concentration of 0.00045 weight %. The reading was performed as described in Example 3 using both the high (sensitivity 108V) and low (sensitivity 120V) standard method. The addition of the surfactant enhanced wetting of the wells and Table 8 shows a summary of the results for known samples at 0.1 and 100 ppb.

TABLE 8

| Sample | Number of wells | Mean (ppb) | Standard Deviation |
|---|---|---|---|
| 0.1 ppb | 82 | 0.091 | 0.031 |
| 100 | 6 | 100.404 | 1.624 |

EXAMPLE 7: SELECTING OPTICAL FILTERS FOR IMPROVING THE SENSITIVITY OF BERYLLIUM ANALYSIS BY OPTICAL FLUORESCENCE

Figure 4:
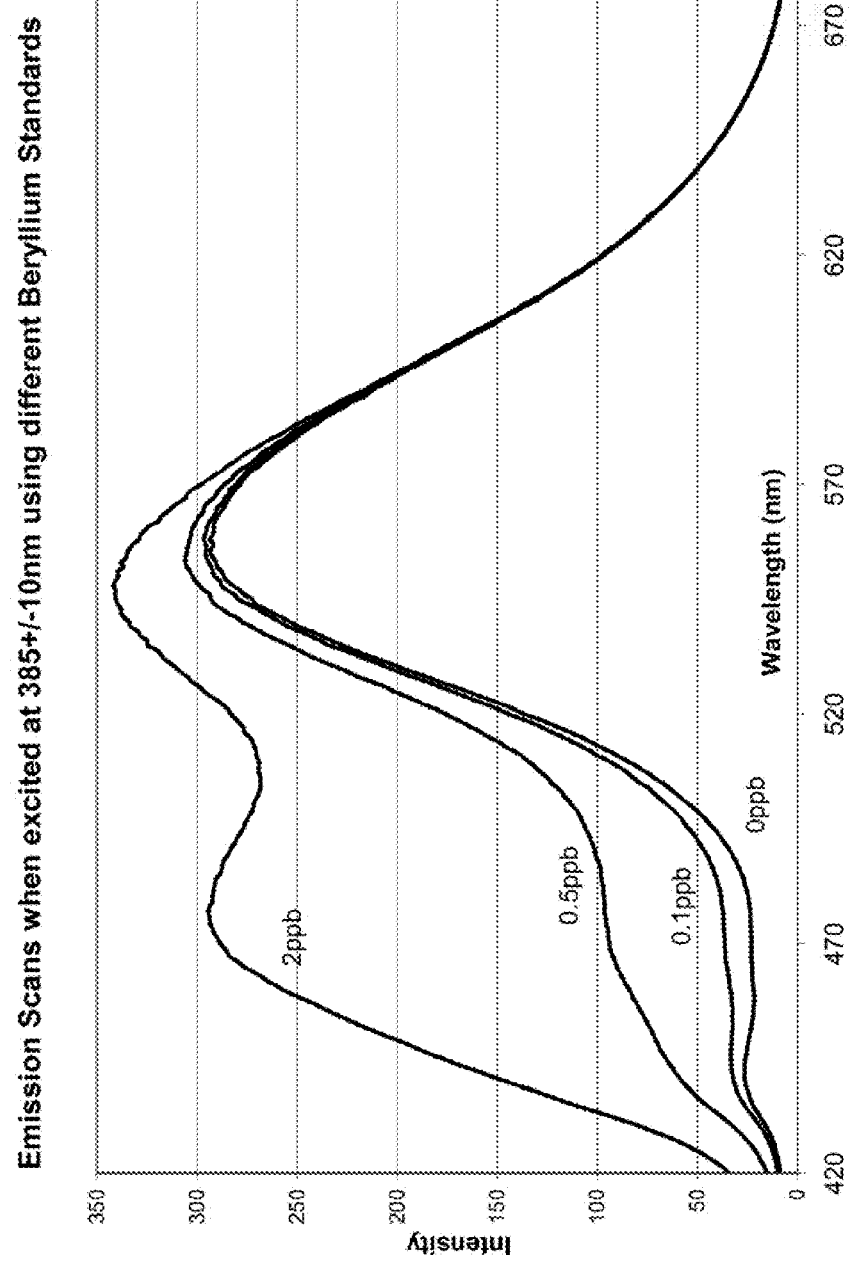
FIG. 4: Change in fluorescence emission for different concentrations of beryllium when excited by optical radiation of 385 nm and a bandwidth of 20 nm (i.e., ±10 nm centered around 385 nm)
Figure 6:
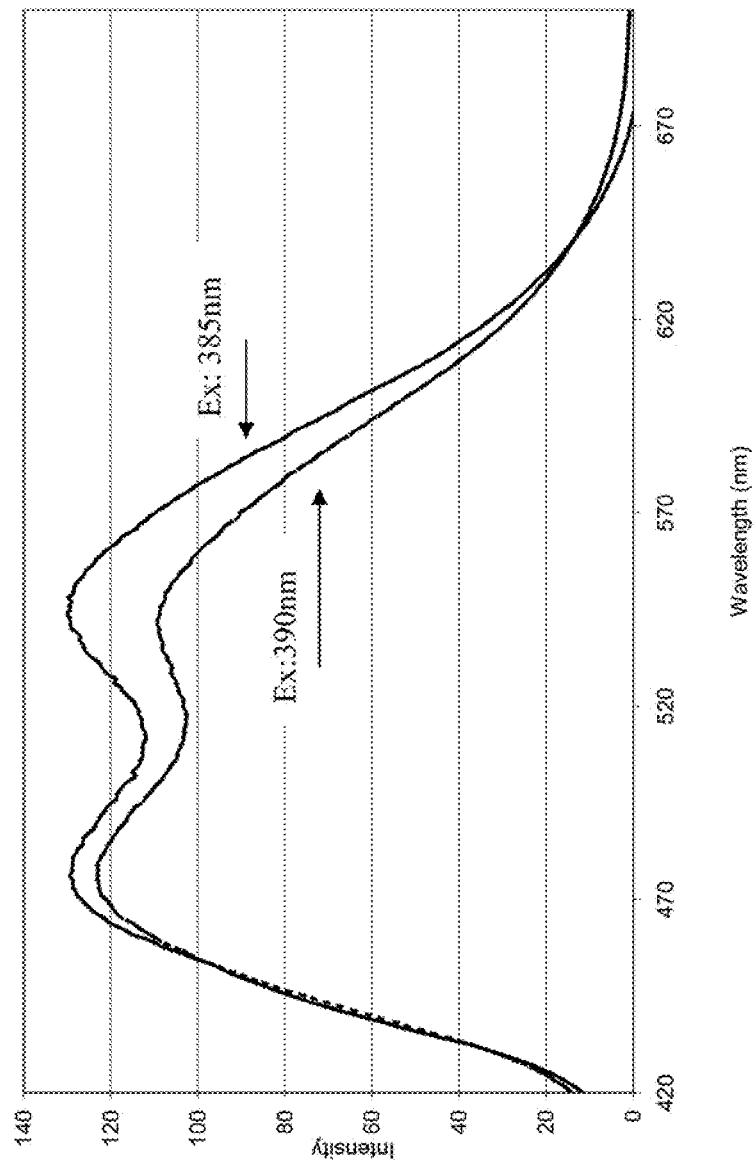
FIG. 6: Emission spectra of a beryllium assay when the sample is excited by 385 nm and by 390 nm optical radiation, the band width for both is ±10 nm.

Solutions with various beryllium concentrations were made as in Example 3 and evaluated in 4 ml plastic cuvettes on a Shimadzu (Columbia, Md.), Model RF5301PC fluorometer. These results are shown in FIG. 4 for a few of the concentrations. The emission at 476 nm is used to quantify the results. This spectrum was generated by using excitation at 385 nm±10 nm. The peak at about 550 nm is due to the binding of protons. The rationale for the choice of excitation wavelength can be seen in FIG. 5. This figure shows the intensity of the emission peaks at 476 nm and 545 nm as the excitation wavelength is changed. The peak at 476 sees maximum excitation from radiation at 385 nm, whereas the peak at 545 nm sees the maximum excitation from 370 nm. Since, for quantitative aspect it is important to curb the peak at 545 nm, the figure also shows the ratio of the excitation at 476 vs excitation at 545 nm. This ratio peaks at 387 to 390 nm. This means if this wavelength was used for excitation, one would get the highest signal at 476 nm when relatively compared with the signal at 545 nm. It can be seen from the excitation curves in FIG. 6, one is able to curb the peak at 545 nm while only losing a bit of intensity at 476 nm. Thus the most preferred excitation should be centered at 387 to 390 nm, however a preferred range for the excitation peak is between 375 to 395 nm Thus the range from 375 to 395 is preferred for exciting the peak at 476 nm for quantitative purposes. Further it is preferred that for reading one should look at most preferably between 470 and 480 nm to read the peak at 476 nm, although one may consider the range of 460 to 490 nm. A preferred bandwidth for excitation is 25 nm or less and for emission the preferred bandwidth is 25 nm or less. These ranges may be used for both cuvette and plate readers. These peak values and bandwidths can be used for specifying the optical filters used for this purpose. For filter based instruments, filters meeting these specifications are available from a variety of sources such as Semrock (Rochester, N.Y.), Omega (Brattleboro, Vt.) and Barr Research Associates (Westford, Mass.). A preferred transmission of the filters is greater than 50%, and more preferably in the range of 80 to 95%. The edge should be sharp dropping from about maximum to 99% of the minimum within 5 nm.

EXAMPLE 8: IMPROVED FILTRATION SYSTEM

With some multiwell filter plates the filtration process requires a sealed cover positioned over them (Type A plates), while with some other filtration plates (Type B plates) no such cover is necessary. The choice of filter plates depends on the type of filtration media required and their cost. As an example, the Seahorse Bioscience (North Billerica, Mass.) filter plates, part# F20062, filter well without a covering on top even when the liquid levels are different or some wells are empty. The filter plates used had 96 wells with a 2 ml well capacity and a 0.45 µm hydrophilic polyether sulfone (PES) membrane located at the bottom of the well. These plates were tested by pipetting one ml of water in 10 wells, and it was found that up to 45 minutes no water passed through the membrane in any of the wells, thus this was type B or non-leaky filter plate. During this testing process no vacuum was applied to assist filtration.

Acroprep™ 96 Filter Plate (part number 5052) purchased from Pall Corporation (Ann Arbor, Mich.) required a cover which is explained below. This had a hydrophilic polypropylene membrane in wells with a pore size of 0.2 µm. When one ml of water was placed in 10 wells, the water started passing through the filter in the first well after about 31 s, and all of them were passing some water in about 45 s. Since no vacuum assist was applied, this type of plate was considered a leaky plate or Type A.

An automated filtration system was implemented using the current innovation on a Janus™ automated liquid handling workstation from Perkin Elmer (Waltham, Mass.) with a leaky filter plate. This system was used to automate the procedure for beryllium analysis by fluorescence as provided in the NIOSH and ASTM procedures for wipes and air filters. The vacuum filtration system was also provided by Perkin Elmer. The filter plate was a 96 well plate with well capacity of 1 ml each and used 0.2 µm hydrophilic polypropylene filters in these wells. This was purchased from Pall Corporation (Ann Arbor, Mich.) as Acroprep™ 96 Filter Plate (part number 5052). The filtrate was collected in a 96 well plate placed below the filter plate which were 1 ml capacity Costar® plates (Corning, N.Y.) with a product number of 3959. To ensure that the filtering process was consistent, each of the well openings at the top were sealed, we used a thin silicone membrane (first flexible membrane) which had a durometer hardness of Shore A10 and a thickness of 0.25 mm. this was backed by a general purpose cellulosic sponge as "second flexible membrane" (this open cell sponge is usually used for cleaning) in a thickness of about 1.8 cm (ACE brand purchased from Ace Hardware (Oak Brook, Ill.)) with a product number 10419, and then by placing a dead weight of 300 g with an area of about 7.3 cm×11.3 cm. The filtration process was tested by using about 0.9 ml of water in each of the wells. This process worked very well and no drops were seen hanging at the bottom of the Filter Plate after the filtration process concluded. In another experiment when the silicone sheet was replaced by another silicone sheet of the same dimensions but with a durometer hardness of Shore A20, similar results were seen. When the filter well plate was left open at the top, drops were seen hanging at many of the well tips at the bottom of the wells at the end of the filtration process. Other membranes were also evaluated as discussed below. The hanging drops were seen when only the first flexible membrane was used which was a Viton® rubber sheet in a durometer hardness of 75 A. Various thicknesses (0.8 mm, 1.6 mm and 2.4 mm) of this elastomer were tried without success. Cork sheet in a thickness of 2 mm and silicone elastomer in a thickness of 1.6 mm (shore A 40) when used as only the first flexible membrane also did not yield satisfactory results. In another experiment the silicone first membrane was backed by a soft 6 mm thick closed cell polyethylene foam sheet (stiffness was about 4-6 psi for 25% deformation) and then with a 6 mm thick Viton® sheet of durometer hardness 75 A along with a dead weight of 300 g made out of aluminum, all of which had a cross-section area to cover the filter plate below without hitting the edge ridges of the filter plate. This combination also worked very well with a vacuum of about 53 cm mercury. In yet another experiment Viton® sheet as above and the PE foam as above were purchased with adhesive back. The Viton® was bonded to the steel plate and the foam sheet was bonded to the Viton®. This bonded combination with a thin silicone first membrane described above also worked very well. This invention is particularly useful when filtering those well plates, where the liquid levels in them is different, or in some no liquid is present.

EXAMPLE 9: PROTOCOL FOR CALIBRATING SYRINGES ON THE HT EQUIPMENT

A protocol, Syringe Calibration Quarterly Verification.MPT, was written using WINPREP® software (Perkin Elmer Corporation, Waltham, Mass.) specifically for the high throughput analysis of beryllium samples. The protocol was designed to identify problems with the syringes dispensing incorrect volumes during the analysis. This was achieved by writing a protocol, Syringe Calibration Quarterly Verification.MPT, where known values are dispensed by the syringes and checked by weighing. Volumes used were particular to the high throughput analysis for beryllium and were in the range of 10 µl-5000 µl. Any protocols that that are done on the liquid handling system to move liquids include performance files. Performance files contain important information for accurately pipetting, such as aspirate speeds, dispense speeds, air gap volumes, syringe pump speeds and volume compensation criteria. Since the volumes used for the high throughput beryllium analysis cover such a broad range, one performance file cannot be used for all of the volumes pipetted. The dispensing and aspirating volumes are much more precise and accurate using a separate, custom performance file for each range of volumes used. If the results of this protocol show that the syringes for a certain tested volume are over or under dispensing, the volume compensation criteria in the performance file can be adjusted accordingly to fix the discrepancy. An example of the volume dispensing range and accuracy using this protocol is shown in Table 9.

TABLE 9

| Syringe # | Volume (µl) | Actual Volume Dispensed (µl) | % Yield | Average Volume (µl) | Standard Deviation | % RSD |
|---|---|---|---|---|---|---|
| 1 | 50 | 50.48 | 100.96 | 49.97 | 0.4859 | 0.9724 |
| 2 |  | 49.53 | 99.06 |  |  |  |
| 3 |  | 50.29 | 100.58 |  |  |  |
| 4 |  | 49.58 | 99.16 |  |  |  |
| 1 | 575 | 578 | 100.46 | 576 | 1.6330 | 0.2835 |
| 2 |  | 576 | 100.15 |  |  |  |

TABLE 9-continued

| Syringe # | Volume (µl) | Actual Volume Dispensed (µl) | % Yield | Average Volume (µl) | Standard Deviation | % RSD |
|---|---|---|---|---|---|---|
| 3 |  | 574 | 99.88 |  |  |  |
| 4 |  | 576 | 100.15 |  |  |  |
| 1 | 800 | 803 | 100.36 | 800 | 2.1602 | 0.2700 |
| 2 |  | 799 | 99.84 |  |  |  |
| 3 |  | 798 | 99.81 |  |  |  |
| 4 |  | 800 | 99.95 |  |  |  |
| 1 | 1007 | 1010 | 100.33 | 1007 | 2.1602 | 0.2145 |
| 2 |  | 1006 | 99.86 |  |  |  |
| 3 |  | 1005 | 99.79 |  |  |  |
| 4 |  | 1007 | 99.99 |  |  |  |
| 1 | 5000 | 5037 | 100.74 | 5021 | 12.4466 | 0.2479 |
| 2 |  | 5023 | 100.45 |  |  |  |
| 3 |  | 5008 | 100.16 |  |  |  |
| 4 |  | 5015 | 100.29 |  |  |  |

EXAMPLE 10: ALTERNATIVE METHOD OF PREPARING CALIBRATION STANDARDS: MIXING OF THE FINAL CALIBRATION STANDARDS DIRECTLY IN THE FINAL 96 WELL PLATE

Figure 7:
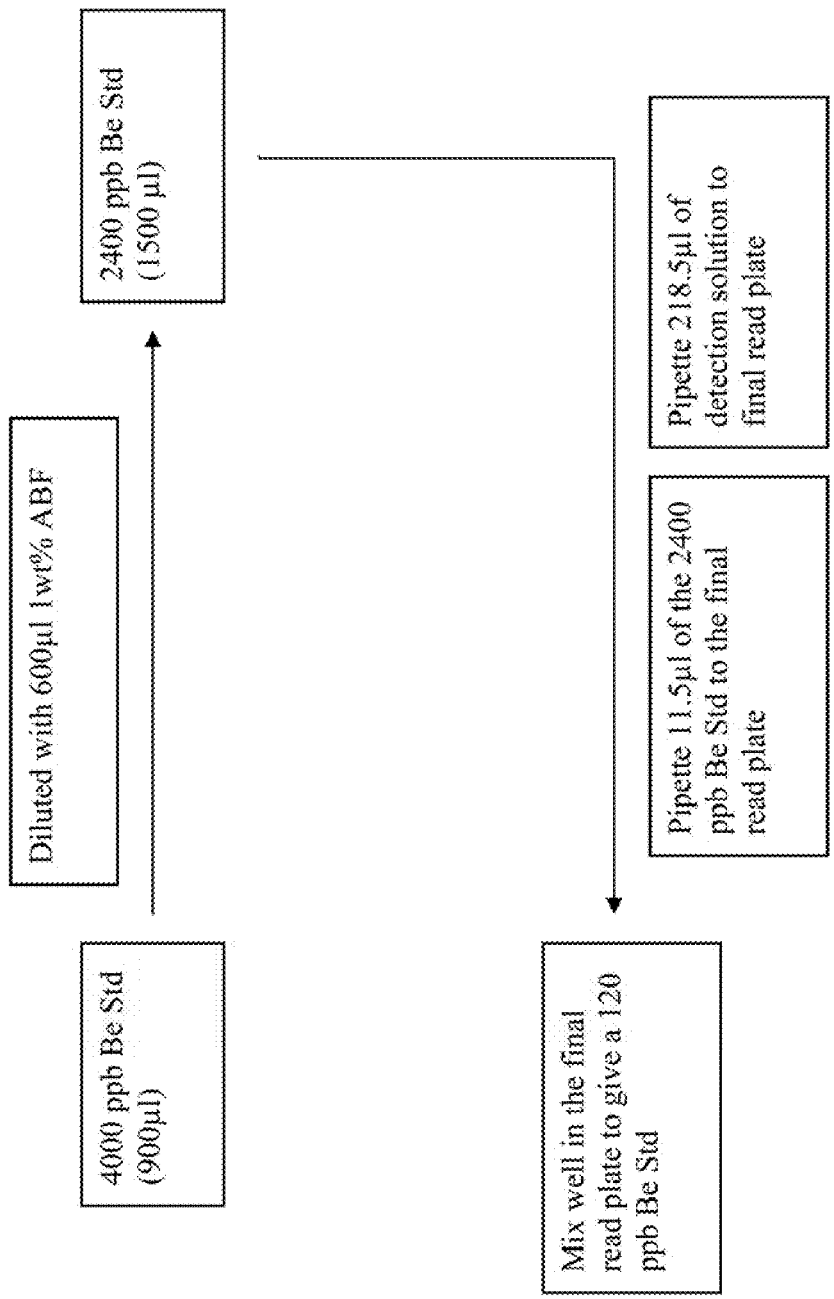
FIG. 7: A flowchart for a method to prepare calibration standards.

In the high throughput analysis of beryllium, calibration standards are prepared in order to calibrate unknown samples. One routine for this using serial dilution was described in Example 3. An automated protocol, "New 20× Calibration Stds 2-18-10.MPT", was written to make the high throughput analysis of beryllium more efficient by using less of the detection solution through mixing the final calibration standards directly in a 96 well plate. This is illustrated by comparing the standard process and the more efficient process using this new protocol. In the standard protocol the calibration standards are prepared using a serial dilution and the detection solution used for each standard is 1007 µl. In the new protocol the total solution volume for each well was 230 µl of which the detection is 218.5 µl and the balance is beryllium containing standard. Pipetting less of the detection solution not only saves on the amount of detection solution used, but it takes less time to aspirate, dispense and mix the standards. A unique aspect of this new protocol is that the calibration stock solutions are no longer prepared by serial dilution. Instead each stock solution is prepared in a larger volume by direct dilution from either a 4000 ppb or a 1000 ppb standard solution. From these larger volumes, the calibration standards with detection solution are prepared directly in the 96 well plate with elimination of the filtration step. A slow mixing step is used to mix the samples. Table 10 lists an example of the mix ratios for obtaining the standards and FIG. 7 shows how a 4000 ppb standard is used to create a final calibration standard of 120 ppb Be. Using this procedure the concentration of the standards and ABF can be varied to give the desired set of standards.

TABLE 10

| Calibration Stock Solution Diluted with ABF (ppb) | Calibration Stock Solution Diluted with ABF (µl) | ABF Diluent (µl) | Final Calibration Stock Solution Prepared (ppb) |
|---|---|---|---|
| 4000 | 900 | 600 | 120 |
| 4000 | 600 | 900 | 80 |
| 4000 | 450 | 1050 | 60 |
| 4000 | 300 | 1200 | 40 |

TABLE 10-continued

| Calibration Stock Solution Diluted with ABF (ppb) | Calibration Stock Solution Diluted with ABF (μl) | ABF Diluent (μl) | Final Calibration Stock Solution Prepared (ppb) |
|---|---|---|---|
| 1000 | 450 | 1050 | 15 |
| 1000 | 150 | 1350 | 5 |
| 1000 | 60 | 1440 | 2 |
| 1000 | 15 | 1485 | 0.5 |

EXAMPLE 11: OPTIMIZING ROUTINES TO USE TIME EFFICIENTLY DURING THE WAITING PERIOD ASSOCIATED WITH THE FILTERING PROCESS

Figure 8:
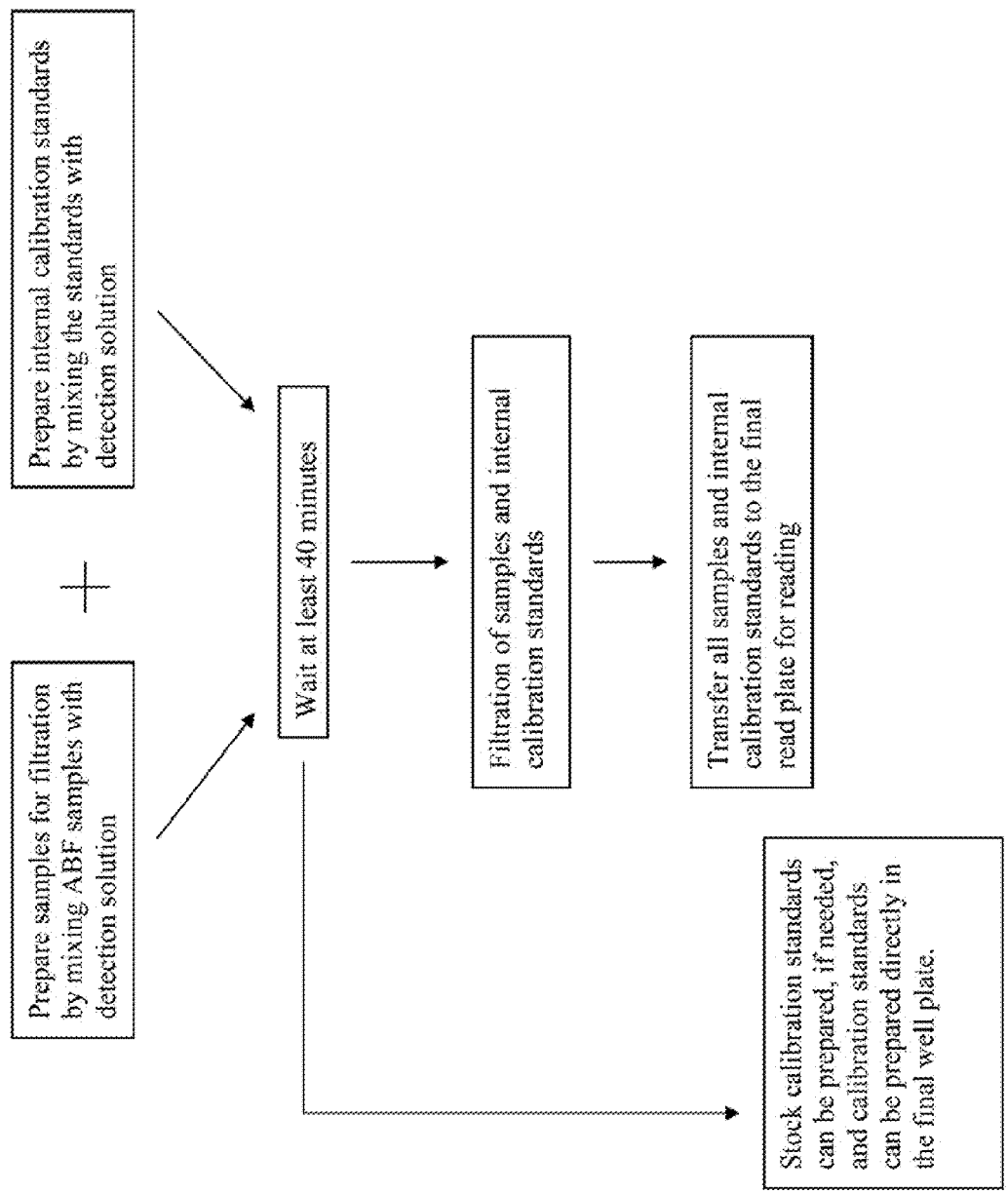
FIG. 8: A flowchart for running programs to increase process efficiency.

Filtering of samples is required in some processes due to the presence of impurities, such as iron and titanium, which can interfere with the fluorescence analysis for beryllium by giving a yellow color. Due to the high pH of the detection solution, these impurities precipitate out over time. This precipitation process can take up to four hours. This wait time was significantly reduced, from four hours to forty minutes, by changing the filtering membrane from nylon to polyether sulfone (PES) or hydrophilic polypropylene with a pore size of 0.45 μm or smaller. This protocol further improved the efficiency of the high throughput analysis of beryllium by allowing optimum use of the wait time, forty minutes, in the filtration step. During the wait time, stock calibration standards are prepared and used to mix the calibration standards directly in the final read plate instead of using a separate standard preparation protocol. This allows the standards to also skip the filtration step, thus saving another 5-10 minutes, since they did not contain yellowing or any particulate impurities. A schematic of this single protocol is shown in FIG. 8.

EXAMPLE 12: INCREASING SAMPLE THROUGHPUT EFFICIENCY BY READING SAMPLES IN A PLATE AGAINST ANOTHER PLATE WITH CALIBRATION SAMPLES

For example, a 96 well plate can be prepared that contains calibration standards, known "check standards" and unknown samples and this plate can be used to generate a standard curve. The next 96 well plate prepared can contain only a few known "check standards" and can accommodate more samples, as it will be read against the calibration curve generated from the first plate. Several additional plates (e.g. two to ten) can be prepared and read against the calibration curve produced from the first plate as long as the "check standards" are within a predetermined compliance. This can be done differently on different types of readers, however, one way of doing this on the Biotek Synergy 2 reader is by using the "Multi-Plate Assay Protocol" rather the "Standard Protocol" which is used when all the samples and the calibrations and checks are on the same plate. This allows one to set the gain to the desired reading for the standards in the first plate and then retain those settings for the reading of each additional plate. However, it is important to have several known "check standards" in each of the additional plates preferably in different places to make sure that there is no problem seen with drift or evaporation. It is especially important that these known "check standards" contain at least several low concentration standards (preferably between 0.5 ppb and 2 ppb of beryllium when using the standardized optical fluorescence test methods) and preferably a blank is also included. This is because it is the low concentration standards that are more likely to see large changes due to evaporation or drift. This will save time and allow the user to process more samples since the calibration standards make up 16 spots in the well plate that can now be filled with samples. It is important to know that the well openings at the top of the plates must be well sealed after preparation if they are to be kept for any amount of time before reading, as each well contains only 230 μl of solution and evaporation can be a problem and could also attract contamination.

EXAMPLE 13: RAPID REPLACEMENT OF DISPENSING TUBING

A problem with working with automated dispensing systems is contamination of the dispensing tubing which is used also as a pipette tip. If the contaminant cannot be removed by washing treatment then a costly and time consuming replacement of the tubing is required. This example relates to a novel process of partial replacement of the tubing where only the contaminated area is removed or a rapid replacement of complete tubing. The contamination in the tubing is unique for environmental analysis where the system is so configured that a limited number of tips, usually eight or less, are used to pipette a large number of samples, where the number of samples exceeds the number of tips by a factor of two or more. Thus it requires washing of the tips after pipetting each of the samples so that there is no carryover from the previous sample. The plastic tubing used to connect from the pump is tapered at the end which serves as the tip. The environmental samples that are typically bulk (e.g., soil, dust, sludge) or collected on wipes or filters are usually added and mixed with an extraction or a dissolution solution, which is typically acidic, so as to extract the desired contaminant into the liquid phase. It is this liquid phase that is then pipetted and processed for analyzing the samples. In addition to the contaminant, the environmental samples may contain other inadvertent additives such as oils, greases, particles of insoluble materials (e.g., hair, fibers, etc). When the environmental samples are pipetted, some of these inadvertent additives are also removed, and these may deposit on the interior walls of the tubing. These deposits are difficult to remove using the automated washing that is done after each pipetting step. With time they deposit on the tube and change the frictional characteristics of the wall. They may also become traps for the environmental contaminants in the sample. Thus periodically it is desirable to replace the plastic tubing that forms the tip and connects to the pump. However, replacing the entire tubing (see Example 3, the tubing length for this example was 12 feet) could be time consuming as typically in these automatic dispensers the tubing is carefully threaded through many slots and bearings within the chain to ensure that these do not entangle with each other or themselves during operation. There are two ways to address this issue, one is to remove or reduce the slots so that the tubing passes through an open chain so that it is easy to replace them. In our experiments we found that even if we removed the slots in the chain, the instrument worked fine and the tubes could be replaced in less than $1/4^{th}$ of the time. Another way is to change only the section of the tubing which sees the contamination. The section length that needs to be changed is determined by the maximum sample volume that is pipetted and then depending on the tube diameter, calculating the length of the tube that has the potential to be contaminated. This volume for this specific case was 1 ml (see Example 3, the routine for Plate Preparation and Analysis, step 17) which corresponds to a length of 57 cm for the tube with an internal diameter of 0.15 cm. Once the contamination length of the tube is known, the replacement length is calculated to be slightly longer. A practical number is about 2 to 10% in excess of the contaminated length. One needs to them ensure that the splicing mechanism used should be such that the joint does not trap bubbles as that can influence the dispense accuracy. Further, the joint should be such that neither the type nor placement of the joint in that part of tubing section will interfere with the movement through slots, chains and bearings), and further it has an easy access at that point. We ascertained that a good splicing point is between 60 to 120 cm from the dispensing tip for the Janus instrument to be adapted for the method for beryllium analysis. For connecting the two ends of the spliced tubing, we used low profile fittings that were inverted cone fittings and a female to female two way coupling from Diba Industries, Inc. in Danbury, Conn. Thus only a section of the tubing that was past this splice point could be changed more frequently with less downtime, typically in about $\frac{1}{4}^{th}$ the time Using this modification no leaking or air entrapment was seen in the connected tubes. This procedure was repeated multiple times with similar results.

EXAMPLE 14: USE OF AN INSTRUMENT USING TUNABLE MONOCHROMATOR RATHER THAN USE FIXED OPTICAL FILTERS

Experiments were done using a Spectramax M5 Microplate Reader from Molecular Devices (Sunnyvale, Calif.). The unique aspect of the Spectramax M5 is that is uses dual monochromator optics instead of fixed excitation and emission filters. This feature allows the user to examine any number of different wavelength combinations. In this example, a set of beryllium standards using a 20× dilution (1.9 ml detection (comprising HBQS dye) solution+0.1 ml beryllium standard) was manually prepared following the procedure of standardized method for detecting beryllium by optical fluorescence. The final beryllium standard concentrations prepared were 0, 0.05, 0.1, 0.5, 2, 10, 40, 100 and 200 ppb. An excitation spectra was first taken while monitoring the integrated emission in the region of 478 nm with a band pass of 15 nm for each of the different standards. The purpose of this experiment was to see at which excitation wavelength most emission is observed in the desired wavelength region. This allows one to optimize the excitation wavelength at which most emission occurs. The results are shown in FIG. 9 the intensity on the y axis represents the intensity of the observed emission when the sample is irradiated with that excitation wavelength.

From this data the excitation peak is found to be between 365 nm and 390 nm. Based on these results an excitation wavelength of 380 nm was chosen with a bandwidth of ±4.5 nm (or total bandwidth of 9 nm) and the emission data was collected. The emission spectra for each beryllium concentration was then taken at different wavelengths. The results are seen in FIG. 10.

Figure 9:
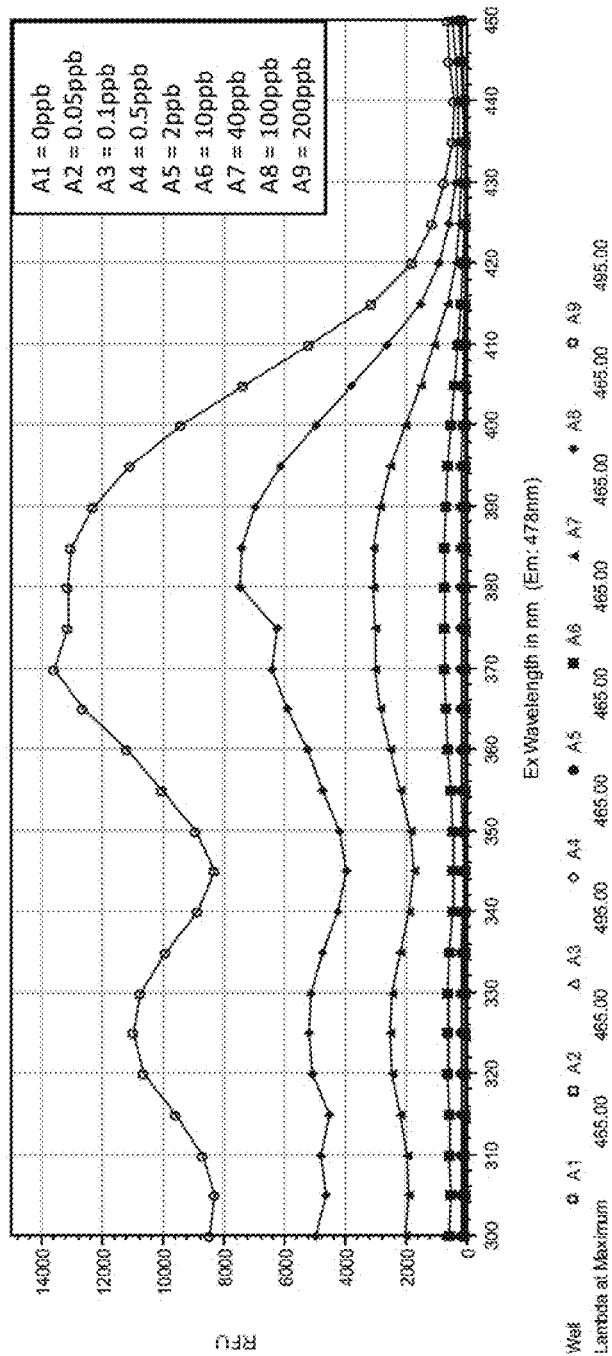
FIG. 9: Excitation spectra of HBQS dye solution with different concentrations of beryllium, these spectra show the effect of emission yield or intensity when the dye solution is excited at different wavelengths, the emission intensity is measured and integrated in the wavelength region of 478 and bandwidth of ±15 nm.
Figure 10:
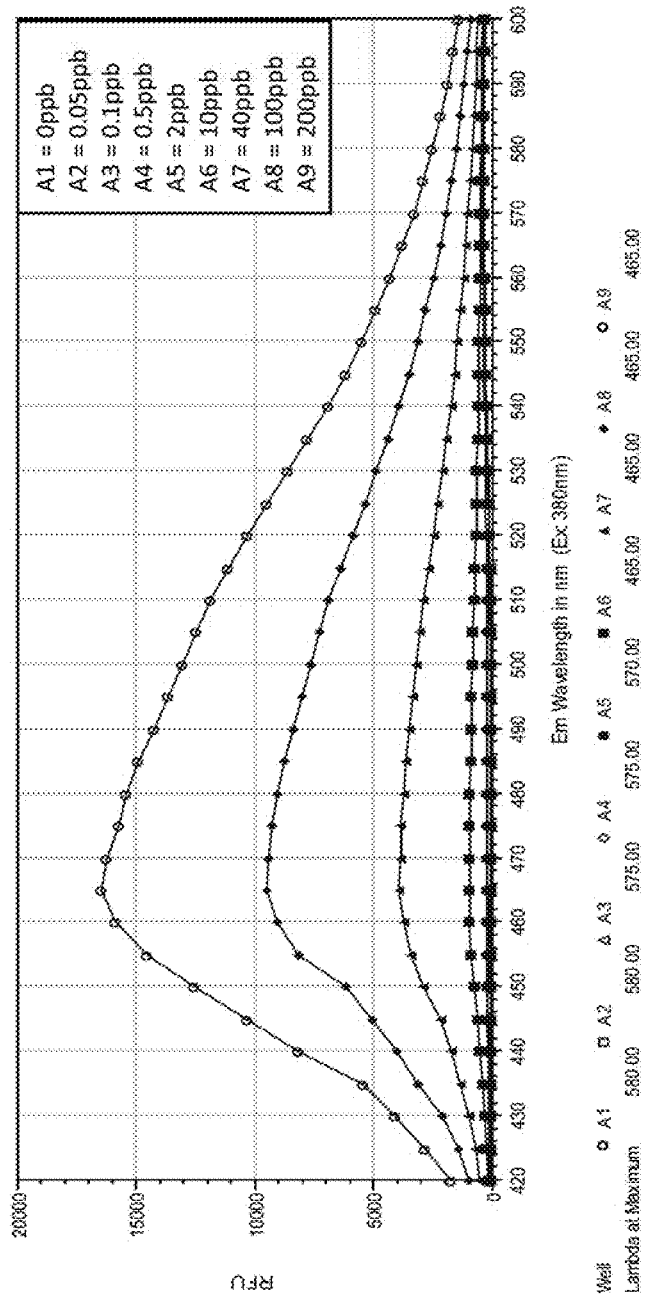
FIG. 10: Emission spectra of HBQS dye solution with different concentrations of beryllium, these spectra show relative fluorescent intensity of these solutions at different wavelengths when excited by using radiation at wavelength of 380 nm and bandwidth of ±9 nm.

Using the guidance from FIGS. 9 and 10, two set of readings of the same plate were taken. These plates have solutions with different concentration of beryllium mixed with with HBQS dye (20× dilution). Different excitation and emission wavelength regions were used. The solutions prepared above were used to calibrate and then evaluated as unknowns showing the readings in Tables 11 and 12 below. The plate was read using one set of parameters first and then was read again using a different set of parameters. The data for the first set of reading with excitation/bandwidth at 365/9 nm and emission/bandwidth at 476/15 nm is shown in Table 11. The standards used to make the calibration curve were 0, 0.05, 0.5, 2 and 10 ppb and the linear correlation coefficient value ($r^2$) was 0.9999. These readings are from averages of eight readings each.

TABLE 11

| Data from Excitation at 365/9 nm and Emission at 476/15 nm | | | | | | | | | |
|---|---|---|---|---|---|---|---|---|---|
| | Be Samples Known Concentrations (ppb) | | | | | | | | |
| | 0 | 0.05 | 0.1 | 0.5 | 2 | 10 | 40 | 100 | 200 |
| Average (ppb) | −0.006 | 0.065 | 0.094 | 0.496 | 2.000 | 9.923 | 37.52 | 109.36 | 215.68 |
| Min. ppb reading | −0.024 | 0.034 | 0.080 | 0.465 | 1.899 | 9.777 | 35.81 | 107.50 | 212.62 |
| Max. ppb reading | 0.017 | 0.121 | 0.109 | 0.515 | 2.308 | 10.05 | 38.18 | 110.83 | 218.61 |
| St. Dev. | 0.011 | 0.027 | 0.009 | 0.014 | 0.131 | 0.096 | 0.734 | 1.199 | 2.097 |

The data for the second reading with excitation at 365±4.5 nm and emission at 476±7.5 nm is shown in Table 12. The standards used to make the calibration curve were again 0, 0.05, 0.5, 2 and 10 ppb and the correlation coefficient value was 0.9999.

TABLE 12

| Data from Excitation at 370 ± 4.5 nm and Emission at 470 ± 7.5 nm | | | | | | | | | |
|---|---|---|---|---|---|---|---|---|---|
| | Be Samples Known Concentrations (ppb) | | | | | | | | |
| | 0 | 0.05 | 0.1 | 0.5 | 2 | 10 | 40 | 100 | 200 |
| Average (ppb) | −0.007 | 0.068 | 0.093 | 0.519 | 2.050 | 10.27 | 38.55 | 110.09 | 215.39 |
| Min. ppb reading | −0.017 | 0.040 | 0.088 | 0.497 | 1.954 | 10.12 | 37.29 | 107.86 | 213.02 |

TABLE 12-continued

Data from Excitation at 370 ± 4.5 nm and Emission at 470 ± 7.5 nm

Be Samples Known Concentrations (ppb)

|  | 0 | 0.05 | 0.1 | 0.5 | 2 | 10 | 40 | 100 | 200 |
|---|---|---|---|---|---|---|---|---|---|
| Max. ppb reading | 0.035 | 0.129 | 0.103 | 0.556 | 2.400 | 10.42 | 39.01 | 111.82 | 220.01 |
| St. Dev. | 0.017 | 0.033 | 0.005 | 0.018 | 0.144 | 0.109 | 0.599 | 1.348 | 2.469 |

This type of an instrument allows one to make changes to the parameters for excitation and emission so as to optimize the sensitivity for customized use or employing the same instrument for analyzing different materials or using different dyes for a given material.

EXAMPLE 15: DYE SOLUTION FOR BERYLLIUM ANALYSIS WHICH HAS LOW FLUORESCENCE BACKGROUND

A buffered HBQS dye solution was made to test for beryllium by optical fluorescence following the guidelines of Standardized test methods. This was made using high purity as received materials and the lysine purity on the material used was stated as 99%+. The dye solution had 63.4 µM 10-hydroxybenzo[h]quinoline-7-sulfonate (10-HBQS) (4)/2.5 mM ethylenediaminetetraacetic acid (EDTA)/50.8 mM lysine monohydrochloride (pH adjusted to 12.8 with NaOH): The solution was prepared by taking 12.5 ml of 10.7 mM ethylenediaminetetraacetic acid (EDTA) disodium salt dihydrate and 25 ml of 107 mM L-lysine monohydrochloride and adding to 3 ml of 1.1 mM 10-hydroxybenzo[h]quinoline-7-sulfonate (10-HBQS). The pH is adjusted to 12.85 with addition of sodium hydroxide and water added to a total of 50 ml. Two different dye solutions were made, one with as received lysine and the other one using a purified lysine. The purification process used was developed by Berylliant Inc (Tucson, Ariz.). A Modulus™ instrument (fluorescence spectrometer) made by Turner Biosystems (Sunnyvale, Calif.) was used to measure fluorescence. This instrument used an LED lamp for excitation with a peak emission of 360 nm and an emission filter specified with a peak transmission at 480 nm±5 nm (full width at half height), with transmission at the peak at about 45%. A plastic cuvette with 1 cm path length was filled (2 ml solution) with these solutions and put in the spectrometer. It was found that the sample with purified lysine produced no detectable background whereas with the as received lysine the background signal was high. In order to quantify this background the following procedure was used. The instrument was calibrated using measurement solutions prepared using 20× dilution ratio (0.1 ml of known beryllium containing standard in 1% aqueous ammonium bifluoride solution and mixing this with 1.9% of the dye solution prepared using purified lysine). As specified in the standard test methods measurement solutions comprising 0, 0.5, 2, 10 and 40 ppb were used. Against this calibration a cuvette holding 2 ml of dye solution with various lysines were measured. Three were as received high purity lysines from different suppliers and one had purified lysine which was purified by Berylliant Inc. Three different batches of as received lysine gave values of 0.22, 0.29 and 0.32 ppb beryllium equivalent signals. While the material with purified lysine resulted in a value of −0.01 to 0, which was within the error range of the instrument for measuring "0" value.

In another experiment 1.9 ml of the dye solution (prepared from purified lysine) was taken which read "0" ppb of beryllium. To this was added 18.5 mg of purified lysine. This amount of lysine is the amount typically present in 2 ml of the dye solution. No background was observed, i.e., the solution read "0" ppb beryllium.

As a comparison point another experiment was done where three dye solutions were made in the same concentration of ingredients as described earlier in this example, but using lysine as received and with variations in dye concentration as described below. In one solution the dye was in the usual concentration of 63.4 µM, in the second one it was $1/10^{th}$ of this concentration and in the third one it was left out completely, the relative background fluorescence counts from these were respectively 380, 208 and 185. This shows that the major contribution of background fluorescence is not from the dye, and even eliminating the dye completely would have only halved the background fluorescence. Thus the process to obtain a low fluorescence background dye solution is to use high purity materials as discussed above and not by changing the dye concentration. In addition, when the dye concentration is changed then one deviates from the Standardized methods discussed earlier. Also, the change in background fluorescence that manifests by changing the dye concentration is likely due to the interaction of the dye and the impurities from the other ingredients as no background fluorescence was seen from the experiment above when these impurities were removed.

EXAMPLE 16: SAMPLE PREPARATION AND ANALYSIS OF URANIUM BY KINETIC PHOSPHORESCENCE ANALYSIS (KPA)

Samples can be made robotically and analyzed on a multiwell plate for uranium using KPA. The uranium samples on media are digested by concentrated acids so that the residue containing uranium can be solubilized in dilute acids. Many samples of sample residue can be put in vials in a tray and brought on the deck of an automated robotic unit (e.g. Janus system from Perkin Elmer). Both dilute nitric acid and the phosphate buffer can be made available as deck fluids just as for beryllium analysis these fluids were dilute solutions of ABF and the HBQS dye solution. The measurement can be done on a plate reader, where most companies make plate readers to measure luminance, e.g. Biotek's models Synergy™ 2SL, H4, H1, Hx, H1m etc. Specifically, the steps are:
  a. Addition of 0.5M $HNO_3$ to digested samples
  b. Mixing step for dissolving the sample in the acid
  c. Passing the samples (or filtering) through columns to remove interfering elements.
  d. Addition of phosphate buffer (1M $H_3PO_4$ solution) to sample solution (proportion is typically 1 ml of uranium solution with 1.5 ml of phosphate buffer)
  e. Preparation of 96 well plate f. Measurement of the well plate
g. Data analysis The excitation of phosphorescence is done at 425 nm and emission is monitored at 525 nm. A typical bandwidth for excitation is 2.5 nm and emission bandwidth 20 nm. These bandwidths and peak positions can be further optimized easily by using a variety of optical filters or using instruments which have wide spectral capabilities or choose instruments with monchromators to pick both the peak positions and the band width as was shown for fluorescence in Example 14. One has to be careful that the specificity for excitation of uranium is maintained. Each sample is subjected to repeated pulses and the data is averaged and then plotted as $I=I_0 \exp(-kt)$. Where "I", is the observed intensity, "t" is time, "k" is a constant and $I_0$ is the intensity extrapolated to $t=0$. From this data set, initial intensity "$I_0$" is calculated which is then proportional to the uranium concentration. The number of pulses may be any in order to obtain sufficient statistical confidence to obtain the desired detection limits and could run into several hundred to thousands, the pulse width for excitation is usually less than 100 μs and may be as small as 5 μs. The kinetic data of the phosphorescence decay is collected sufficient time after the excitation so that the excitation duration can be fitted to a single decay curve and only captures phosphorescence. The time after excitation after which the data is collected after the excitation period ends (wait time about 2 to 10 times the excitation pulse width) and is collected for sufficient time to get a good trace of the curve for extrapolation as described above. The passing through the column in step "c" above should be explained in more detail. Such columns bind the other elements that may be present in the samples while letting uranium pass through. This procedure reduces interference by the other elements during analysis. Depending on the expected interfering elements such columns are available from Eichrom Inc (Lisle, Ill.). Such filtration media can be introduced in 96 well (or any other count) filter plates or solid phase extraction tubes which can be arranged in an array format and the filtrate can then be obtained in standard well plates located below the filter. Solid phase extraction (SPE) tubes are standard components which are used in chromatography and may even be bought empty in which a desired media can be introduced during the manufacturing process (see Sigma Aldrich located in Milwaukee, Wis. for a catalogue of empty SPE cartridges and those used for a variety of other uses).

EXAMPLE 17: ATTACHMENT OF FLUID LEVEL SENSORS TO THE NON-CONDUCTIVE PIPETTING TIPS OR TUBES

Figure 11:
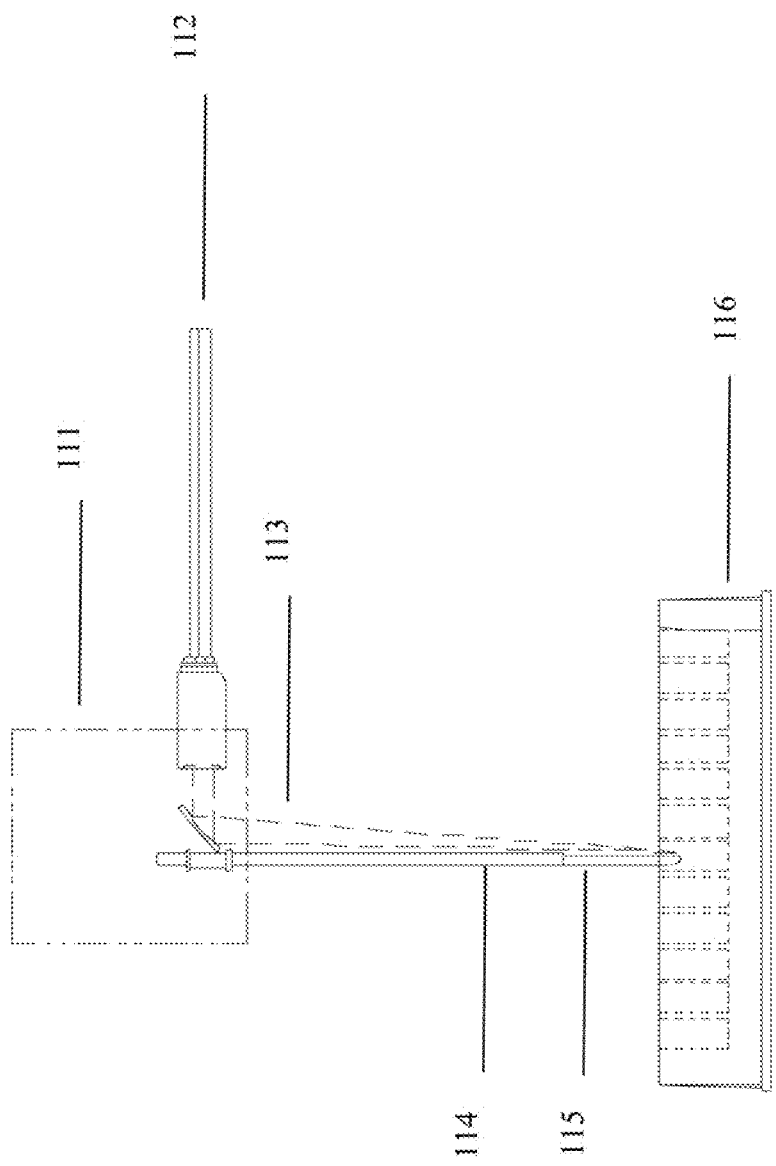
FIG. 11. Shows an schematics of incorporating optical liquid level sensors in pipettes using non conductive plastics tips.

FIG. 11 shows a schematic diagram where an optical fluid level sensor attached to a pipetting tip. The tips (all of them) are usually housed in a block 111. Only one tip is shown. The pipetting tip is a tube 115 that runs through a support sleeve 114. The tip of the pipetting tube is shown in proximity to a multiwell plate 116. The optical sensor is shown as 112, and shows a beam of light as 113 that is focusing very close to the pipetting tip. Typically the sensor head would also be housed in the same block which is used for the tips. The sensor can check the presence of liquid by a change in reflectivity. The sensor can be a reflective sensor type like Keyence Fiber optic unit series FU (i.e. FU40) or a CCD laser retro-reflective like the LV-S41. These units are connected to a small amplifier (i.e. LV-11SB) that could output a signal to the Janus equivalent to the one from the capacitive sensors.

While this invention has been described as having preferred sequences, ranges, steps, materials, structures, features, and/or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the appended claims.

What is claimed is:

1. A method of determining the presence or amount of beryllium or a beryllium compound by fluorescence in a series of liquid samples, wherein the method comprises mixing each of the sample with a solution containing a fluorescent indicator and creating a series of mixtures, filtering the said mixtures through a non-leaky multiwell filter plate and assisting the said filtration process by applying a vacuum to draw the said mixture through the non-leaky filter plate, exciting the filtered solutions by optical radiation and measuring fluorescence signal from the said filtered solutions to determine the presence or amount of beryllium or the beryllium compound.

2. The method of claim 1, wherein some of the liquid samples contain predetermined amount of beryllium, and the method comprises using those liquid samples to provide calibration data for use in measuring fluorescence from the other liquid samples where the beryllium amount is not known.

3. The method of claim 1 wherein at least one of (a) the liquid samples, (b) the solution containing the fluorescent indicator and (c) the mixture of the said liquid sample with the solution containing the fluorescent indicator has a pH lower than 2 or has a pH higher than 10.

4. A method of determining the presence or amount of toxic elements found in environmental or industrial hygiene samples collected from soil, water, air and surfaces, wherein these elements are extracted into an aqueous liquid unless the sample is present in an aqueous liquid form wherein a number of these liquids or mixtures containing the said liquids are filtered through a non-leaky multiwell filter plate and assisting the said filtration process by applying a vacuum to draw the said mixture through the said filter plate into another multiwall plate, and then using the filtrate to determine the presence or the amount of the said toxic elements in the filtrate.

5. The method of claim 4 where the said liquid samples or their mixtures have a pH lower than 2 or has a pH higher than 10.

6. The method of claim 4 wherein the toxic elements are selected from at least one of lead, mercury, cadmium, arsenic, beryllium, thallium, antimony, uranium and selenium.

* * * * *